(12) United States Patent
Newham

(10) Patent No.: US 6,297,738 B1
(45) Date of Patent: *Oct. 2, 2001

(54) MODULAR SYSTEM FOR MONITORING THE PRESENCE OF A PERSON USING A VARIETY OF SENSING DEVICES

(76) Inventor: Paul Newham, 707 Cypresstee, San Antonio, TX (US) 78245

(*) Notice: Subject to any disclaimer, the term of this patent is extended or adjusted under 35 U.S.C. 154(b) by 0 days.

This patent is subject to a terminal disclaimer.

(21) Appl. No.: 09/401,482

(22) Filed: Sep. 22, 1999

Related U.S. Application Data

(63) Continuation-in-part of application No. 08/871,363, filed on Jun. 9, 1997, now Pat. No. 6,025,782, which is a continuation-in-part of application No. 08/708,397, filed on Sep. 4, 1996, now abandoned.

(51) Int. Cl.$^7$ ................................................ G08B 21/00
(52) U.S. Cl. .................................. 340/573.1; 340/573.4; 340/568.1; 340/666; 200/600; 307/116; 307/125; 128/886; 600/595
(58) Field of Search ........................... 340/573.1, 568.1, 340/666, 573.4; 200/600; 307/116, 125; 128/886; 600/595

(56) References Cited

U.S. PATENT DOCUMENTS

| | | | |
|---|---|---|---|
| Re. 29,896 | 1/1979 | Gilcher | 340/562 |
| 4,020,482 | 4/1977 | Feldl | 340/573.4 |
| 4,033,332 | 7/1977 | Hardaway, Jr. et al. | 600/535 |
| 4,146,885 | 3/1979 | Lawson, Jr. | 600/534 |
| 4,179,692 | 12/1979 | Vance | 340/573.1 |
| 4,196,425 | 4/1980 | Williams, Jr. | 340/573.4 |
| 4,212,295 | 7/1980 | Snyder | 128/886 |
| 4,228,426 | 10/1980 | Roberts | 340/573.4 |
| 4,242,672 | 12/1980 | Gault | 340/573.4 |
| 4,293,852 | 10/1981 | Rogers | 340/568 |
| 4,295,133 | 10/1981 | Vance | 340/573.4 |
| 4,381,788 | 5/1983 | Douglas | 600/535 |
| 4,402,560 | 9/1983 | Swainbank | 439/37 |
| 4,474,185 | 10/1984 | Diamond | 600/535 |
| 4,484,043 | 11/1984 | Musick et al. | 200/85 R |
| 4,565,910 | 1/1986 | Musick et al. | 200/85 R |
| 4,583,084 | 4/1986 | Henderson et al. | 340/573.4 |
| 4,633,237 | 12/1986 | Tucknott et al. | 340/573.4 |
| 4,700,180 | 10/1987 | Vance | 340/573.4 |
| 4,858,622 | * 8/1989 | Osterweil | 600/595 |
| 4,907,845 | 3/1990 | Wood | 340/573.4 |
| 4,947,152 | 8/1990 | Hodges | 340/573.4 |
| 5,010,772 | 4/1991 | Bourland et al. | 73/862.04 |
| 5,086,291 | 2/1992 | Schwab, Jr. | 340/604 |
| 5,107,855 | 4/1992 | Harrington et al. | 600/534 |
| 5,137,033 | * 8/1992 | Norton | 128/886 |
| 5,144,284 | 9/1992 | Hammett | 340/573.1 |
| 5,184,112 | 2/1993 | Gusakov | 340/573.1 |
| 5,235,319 | * 8/1993 | Hill et al. | 340/573.4 |
| 5,253,656 | 10/1993 | Rincoe et al. | 600/595 |
| 5,410,207 | 4/1995 | Joseph et al. | 310/328 |
| 5,448,996 | 9/1995 | Bellin et al. | 600/574 |
| 5,471,198 | * 11/1995 | Newham | 340/573.4 |
| 5,494,046 | * 2/1996 | Cross | 600/595 |
| 5,877,675 | * 3/1999 | Rebstock et al. | 340/286.07 |
| 6,025,782 | * 2/2000 | Newham | 340/573.1 |

* cited by examiner

*Primary Examiner*—Benjamin C. Lee
(74) *Attorney, Agent, or Firm*—Cox & Smith Incorporated

(57) ABSTRACT

A capacitive array is housed within a polyester mat or other appropriate nonconductive substrate material which is interconnected with a control module. The control module supplies to the capacitive array a suitable oscillator driver current and concurrently senses capacitance value changes within the capacitive array induced through dielectric shifts within the array brought about by the proximity or absence thereof of the patient's body mass. The monitor/control module generally comprises a power supply, a driver/sensor circuit, a calibration/comparator logic circuit, a system interconnection integrity circuit, and an alarm generation circuit. It may also optionally contain a nurse call relay circuit for interconnection to a facility's nurse call system.

24 Claims, 13 Drawing Sheets

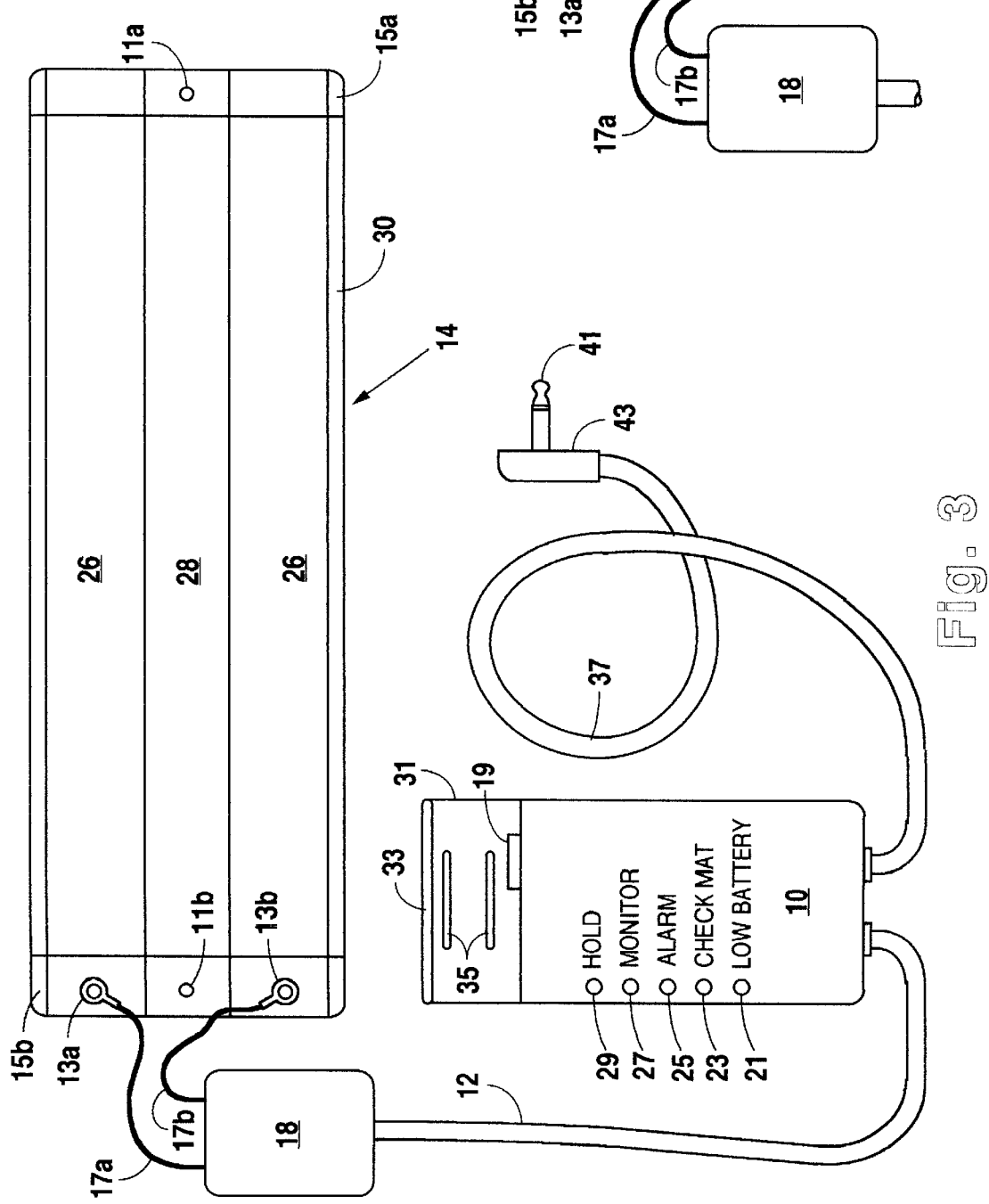

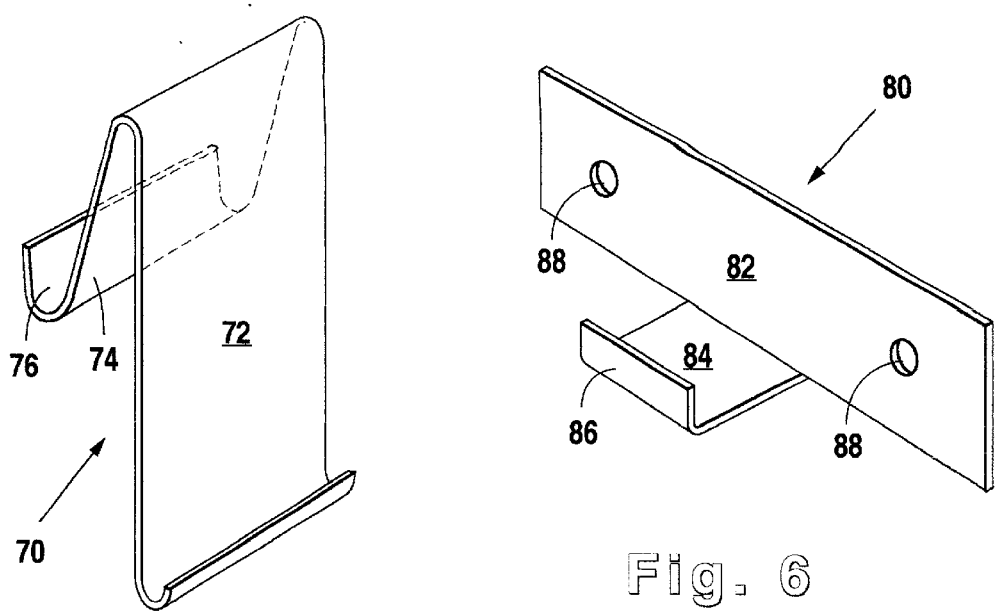
Fig. 5
Fig. 6
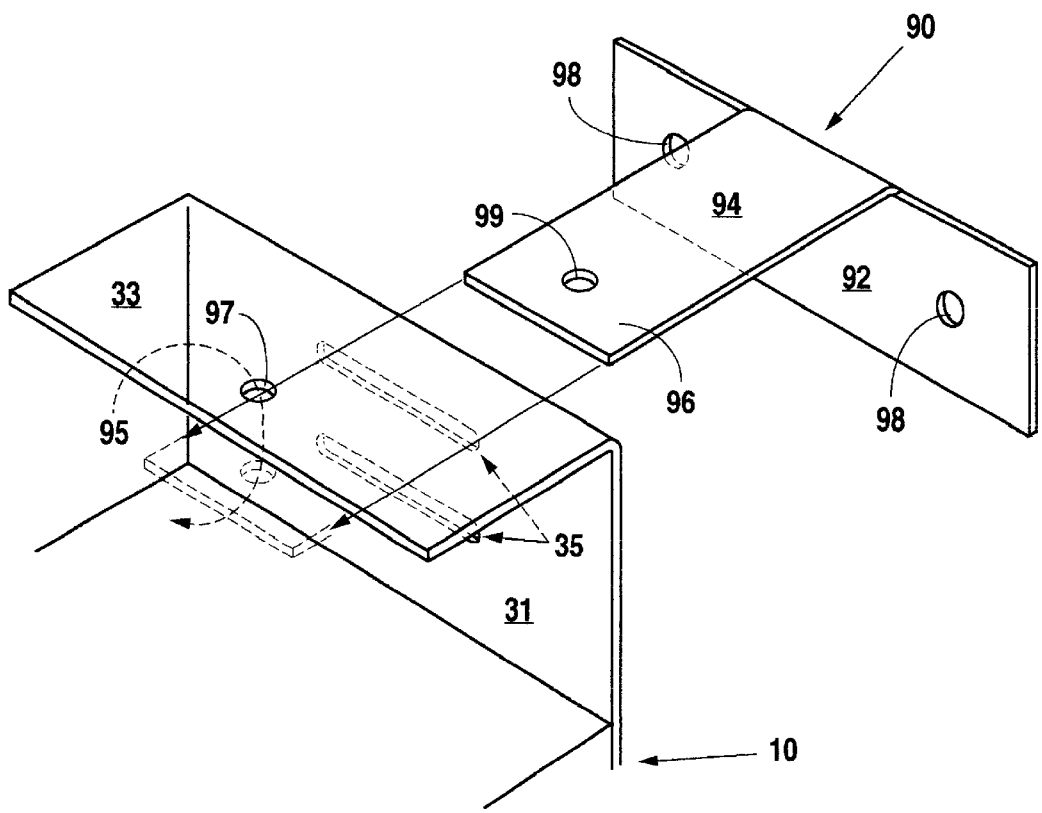
Fig. 7

MODULAR SYSTEM FOR MONITORING THE PRESENCE OF A PERSON USING A VARIETY OF SENSING DEVICES

RELATED APPLICATIONS

The present application is a continuation-in-part of U.S. patent application Ser. No. 08/871,363, filed Jun. 9, 1997, now U.S. Pat. No. 6,025,782, which is a continuation-in-part of U.S. patent application Ser. No. 08/708,397, filed Sep. 4, 1996, now abandoned the disclosures of which are incorporated herein by reference.

BACKGROUND OF THE INVENTION

1. Field of the Invention

The present invention relates generally to devices for the detection of dielectric shift induced capacitive changes. The present invention relates more specifically to the use of such devices for the detection and monitoring of the presence or absence of a person from a medical bed, chair or other support structure so as to insure the safety of a patient occupying such a structure.

2. Description of the Related Art

A problem well known to medical service providers is that of making sure certain patients remain in their medical bed or chair. Reasons for this include the need to quickly locate the patient, administer medical treatment to the correct patient, and the prevention of patient injury. Such knowledge is particularly important when patients have become disoriented due to illness or medication.

Medical bed and chair occupancy monitoring systems have been devised to assist medical providers with monitoring the presence or absence of a person in their bed or chair. Such systems typically are equipped with an alarm or are electronically tied to a common monitoring location, such as a nurses station. Such systems principally use some form of pressure sensitive switch as their key sensing element. U.S. Pat. Nos. 4,484,043 and 4,565,910, both Musick et al, and other similar patents describe switch mechanisms which are used to open and close a circuit to indicate the evacuation of a bed or chair by a patient. In the above described patents, the switch apparatus is housed in a thin rectangular cover which may be placed between the patient and the mattress or between the patient and the seating surface. An alternative version of the above described switch mechanism is placed between the lower surface of the mattress and the upper surface of the bed frame. The switch devices in all of the above described mechanisms are each comprised of two rectangular conductors which run the length of the device, are parallel to each other and lie one on top of the other. The two conductors are separated at both ends by a pliable material such as foam and are held apart from each other through the rigidity of the switching apparatus itself. The switch is activated by the pressure of the patient's body weight on the device, either directly thereon or indirectly through the mattress. Once this weight is applied, the two conductive elements come into contact, the switch is closed, and the system indicates that the patient is in the bed or chair. When the switch is opened by the absence of the patient's weight in the bed or chair, the system then sounds an alarm or sends a signal to the medical facility call system through an appropriate interface.

Such pressure sensitive switching elements, as previously described, suffer from certain inherent problems. Switching elements which are placed under the mattress exhibit extremely limited sensitivity and selectivity in identifying the presence of a patient in the bed. This is due to the fact that the patient's weight in the bed is masked by the mattress itself. This masking effect tends to result in frequent false alarms due to the switch failing to close properly, as well as the failure to generate an alarm when the switch fails to open, even though the patient is no longer in the bed. As for pressure sensitive switches placed between the patient and the mattress or seating surface, they must be extremely thin to afford the patient a reasonable degree of comfort. Although such switches exhibit substantially improved sensitivity and selectivity, the required thinness of the movable switch elements, their supportive structure and the required dielectric space between them causes them to have a considerably limited life. Such switches are, therefore, manufactured as disposable devices whose costs prohibit their broad acceptance and use.

It is, therefore, an object of this invention to provide a proximity induced non-compressive dielectric shift sensing device, which replaces the existing pressure sensitive switches previously described for the monitoring of the presence of a patient in a medical environment. A further object of this invention is to provide such a device which either interfaces with occupancy monitoring control modules already in use or utilizes self-contained control module circuitry and controls.

It is another object of the present invention to provide a proximity induced non-compressive dielectric shift sensing device which may be used as a portable unit, or may be wholly or partly built into or mounted on a medical bed, chair, mattress, cushion or similar structure to sense the presence or absence of a person normally occupying the structure.

It is a further object of the present invention to provide a proximity monitoring device with a limited and controlled range that can reliably detect the presence or absence of a person, thereby decreasing the number of false and unreliable alarms.

It is another object of the present invention to provide a proximity monitoring device which will greatly decrease or eliminate patient discomfort by replacing mechanical pressure sensitive switches in the medical bed or chair with a considerably thinner and more flexible sensing element.

It is a further object of this invention to provide a proximity monitoring device, the sensing element of which will exhibit considerably lengthened service life through the elimination of all moving components within the sensing element.

It is a further object of this invention to provide a proximity monitoring device whose sensing element is inherently simpler in design and to manufacture, and utilizes less raw material, thereby resulting in a lower cost end user product.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

According to the present invention, the foregoing and other objects and advantages are attained by an electronic device able to detect and monitor the presence or absence of a person within a pre-defined space. The device generally comprises a capacitive array housed within a polyester mat or other appropriate nonconductive substrate material which is interconnected with a control module. The control module supplies to the capacitive array a suitable oscillator derived driver current and concurrently senses capacitance value changes within the capacitive array induced through dielectric shifts within the array brought about by the proximity or absence thereof of the patient's body mass. The monitor/control module generally comprises a power supply, a driver/sensor circuit, a comparator/calibration logic circuit, a system interconnection integrity circuit and an alarm generation circuit. It may also optionally contain a nurse call relay circuit for interconnection to a facilities nurse call system.

The driver/sensor circuit provides and senses a suitable current to the capacitive array located in the patient's bed or chair. The driver/sensor circuit is connected to and controlled by a comparator/calibration logic circuit that is most preferably microprocessor based. This logic circuit continually analyzes and optimizes signals received from and generated by the driver/sensor circuit. In this way, the logic circuit defines capacitive value parameters which it interprets to indicate whether a patient is in close proximity to the capacitive array or absent from that array. In such manner, the logic circuit determines the presence or absence of a patient from his or her support structure. Should the capacitive value change and remain at a level indicative of a patient's absence from their support structure, the logic circuit would, after a suitable pre-programmed time delay, instruct an alarm circuit to activate. This alarm activation may consist solely of audible and/or visible alarms on or within the control module or may be directed to a medical facility's nurse call system through an appropriate interface relay circuit contained either within, or remote to, the control module.

In addition to the above described functions, the logic circuit receives continuous data from the control module system interconnection integrity circuit about the continuity of connection between the control module and the capacitive sensor array and, where appropriate, between the control module and the medical facility's nurse call system.

The logic circuit may also, if appropriate, continuously monitor the entire system during utilization for service faults and subsequently generate appropriate alarms.

The apparatus of the invention, uses a proximity induced non-compressive dielectric shift sensing mechanism, and thus reliably detects the presence or absence of a patient from a bed, chair or other support structure, with minimal discomfort to the patient and with a greatly extended sensor element service life.

Still other objects and advantages of the present invention will become readily apparent to those skilled in this art from the following detailed description, wherein multiple preferred embodiments of the invention are shown and described, simply by way of illustration of the best mode contemplated by the inventor for carrying out the invention. As will be realized, the invention is capable of other and different embodiments, and its several details are capable of modifications in various obvious respects, all without departing from the invention. Accordingly, the drawings and descriptions are to be regarded as illustrative in nature, and not as restrictive.

BRIEF DESCRIPTION OF THE DRAWINGS

FIG. 3 is a plan view of the structures of the various components of the present invention.

FIG. 3a is a plan view of an alternative strain-relief structure and function for the mat of the present invention.

FIG. 5 is a perspective view of the wheelchair mounting clip of the present invention.

FIG. 6 is a perspective view of the wall mounting clip of the present invention.

FIG. 7 is an exploded perspective view of a locking embodiment of the wall mounting clip of the present invention.

DESCRIPTION OF THE PREFERRED EMBODIMENT

As generally described above, the device of the present invention has practical application in a number of situations.

The device may be used to monitor the presence of a person, or animal, within a pre-defined space. The invention described may be used in hospitals or other medical facilities to monitor the occupancy of medical beds, chairs or other supportive structures whenever it may be useful to determine the status of occupancy of such structures. In addition to its use as a stand alone system in combination with such structures, it is possible that the sensing element capacitive array, through its inherently long service life, could be embedded in or under the surface materials of bed mattress covers and seating surfaces. In such fashion a medical facility would then only have to supply and interconnect the control/monitor module component. Equivalently, if appropriate, the entire monitoring system could become an integral component of an appropriate medical bed or chair on a permanent basis either by original manufacture or by retrofit.

Outside the hospital area, the present device may be used in nursing homes, intermediate and long-term care facilities, mental hospitals, and other similar institutions needing to track the presence of individuals. The invention is not limited to institutional use, but also has practical application as a single, stand alone device in addition to its potential for becoming a built-in device. Such applications could include in-home health care and presence monitoring for the increasing number of patients who choose to have medical care provided in their own homes.

Figure 1:
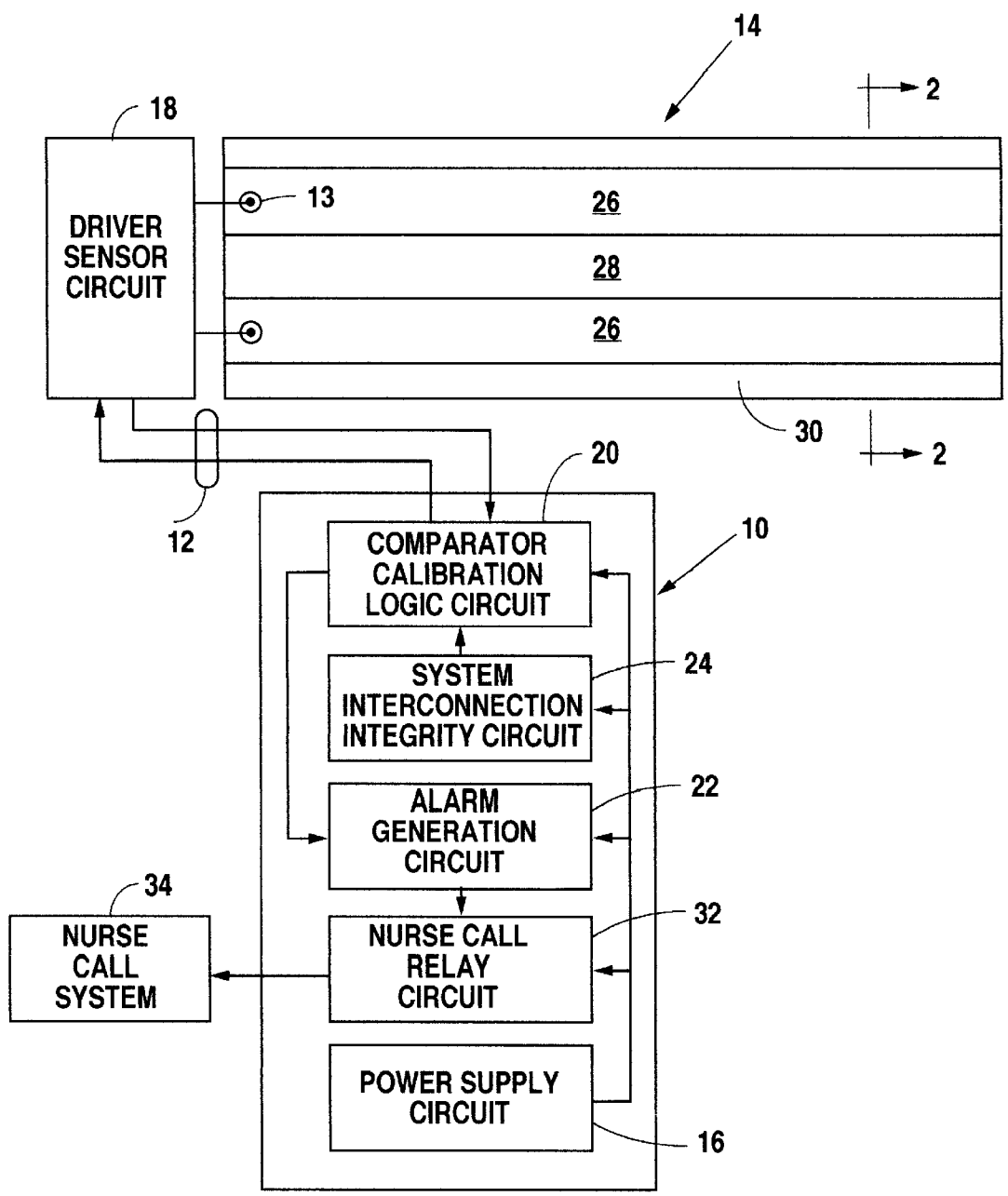
FIG. 1 is a schematic block diagram of a first preferred embodiment of the device's control/monitor module interconnected with a sensing element capacitive array.

Reference is made, therefore, to FIG. 1 for a description of a first embodiment of the current invention. FIG. 1 shows a schematic block diagram showing control/monitor module (10) for the invention interconnected through connections (12) and (13) to one embodiment of sensing element (14). Control/monitor module (10) is made up of several circuit components, including power supply (16). Power supply (16) may consist of an internal power source such as a battery, an external source with an appropriate feed to control/monitor module (10) or any other appropriate source of power known in the art.

Additional circuit components disclosed in FIG. 1 include driver/sensor circuit (18) which provides an appropriate driver current to capacitive array (26) contained within sensing element (14) and concurrently senses capacitive value changes produced within capacitive array (26) through dielectric shifts caused by the proximity or absence of the patient's body mass. Also disclosed in FIG. 1 is comparator/calibration logic circuit (20) which is preferably a microprocessor circuit containing embedded programming suitable to the applications described herein. Comparator/calibration logic circuit (20) interfaces with driver/sensor circuit (18) and alarm generation circuit (22) also contained within control/monitor module (10). In addition, comparator/calibration logic circuit (20) receives input data from system interconnection integrity circuit (24). Comparator/calibration logic circuit (20) continuously monitors the functions of driver/sensor circuit (18) both optimizing the appropriate driver current to capacitive array (26) embedded within sensing element (14) and equivalently continuously monitors and analyzes signal data from the driver/sensor circuit (18).

When the overall system is first activated comparator/calibration logic circuit (20) will determine, through the capacitive value readings it initially obtains, whether the overall system is correctly connected (through data derived from system interconnection integrity circuit (24)) and, if such is the case, then whether a patient's body mass is already proximal to sensing element (14) or if the patient's body mass is absent. From the data derived from such capacitive value readings, comparator/calibration logic circuit (20) will set appropriate capacitive value calibration parameters which, when equaled or exceeded, would indicate the presence or absence of a patient's body mass from proximal contact with sensing element (14). Due to varying environmental conditions (humidity, the presence or absence of other grounded or nongrounded structures, body mass of the patient, etc.), that the capacitive elements (26) embedded within sensing element (14) may be subject to comparator/calibration logic circuit (20) may, as required, adjust the calibration of the capacitive value change parameters.

The principal signal characteristic utilized by comparator/calibration logic circuit (20) is not a direct analysis of capacitive change value derived from sensing element (14), but rather an analysis of the ratio comparing the inherent, resting "unoccupied" capacitance of sensing element (14) examined along side a capacitive value caused through a dielectric shift within sensing element (14) when a patient's body mass comes into contact with sensing element (14). It has been demonstrated through experimentation that a suitable ratio differential that provides accurate and reliable monitoring function by the invention, should be 3 to 1 or more.

Figure 4:
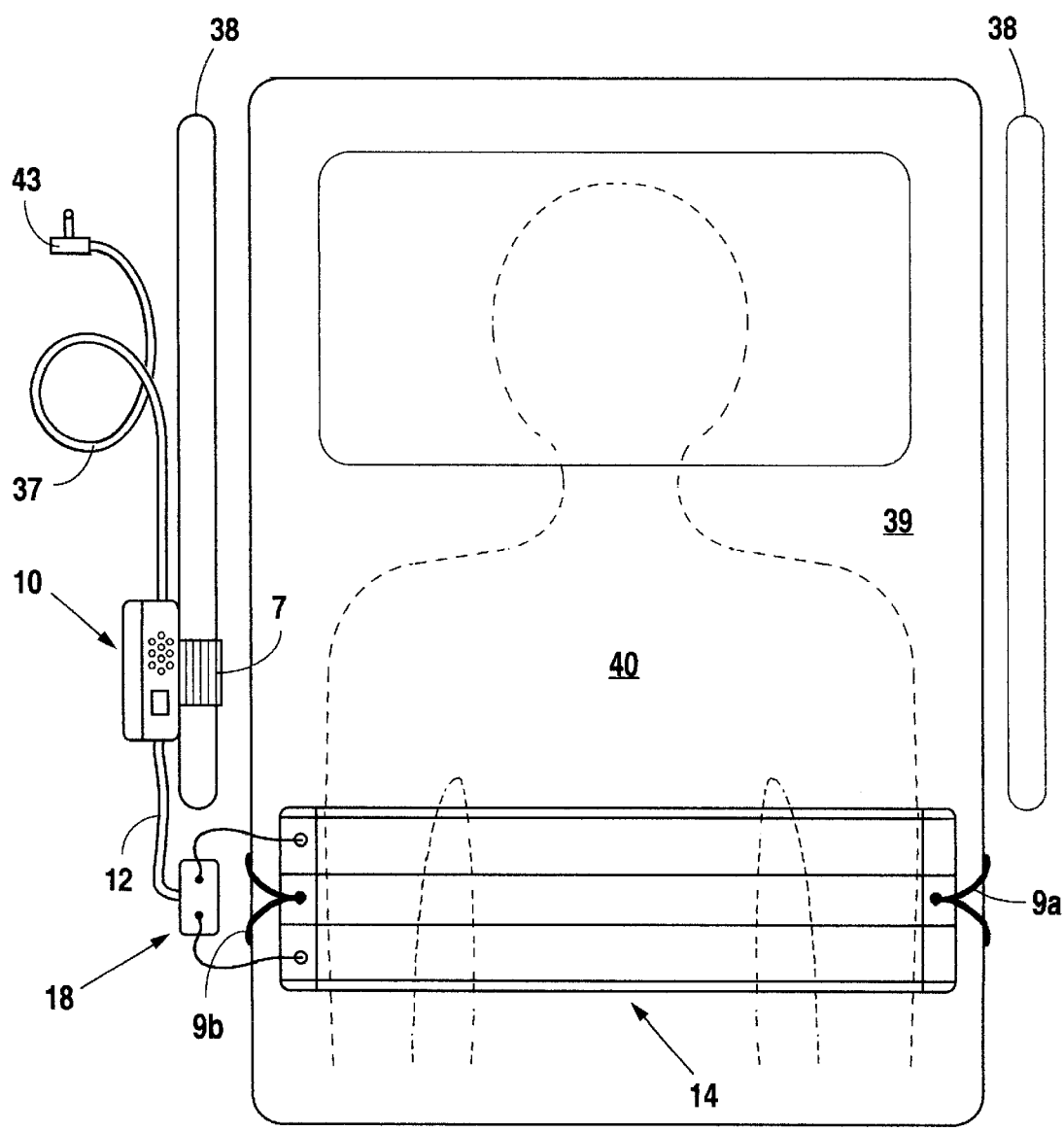
FIG. 4 is a plan view of a preferred location for the sensing element capacitive array as shown in FIG. 1 in relation to a patient in a medical bed.

The first embodiment of the invention utilizing sensing element (14), as shown in plan view in FIG. 1, has experimentally produced an inherent, resting capacitance value of approximately 15 to 20 picofarads when the capacitive array conductive elements are each 2 inches wide by 30 inches long, separated by a dielectric interspace (28) of 2 inches. This overall array is embedded in polyester substrate matrix (30) of sensing element (14) whose overall dimensions are approximately 6 inches wide by 30 inches long. The proximity application of an adult human body mass to sensing element (14) as shown in FIG. 4, has reliably produced capacitive value readings in excess of 250–300 picofarads or a ratio of 12 to 1 or more.

Existing materials utilized for capacitive array (26) manufacture may include copper film, aluminum film, silver/carbon conductive ink, etc. In a preferred embodiment sensing element (14) as shown in plan view in FIG. 1 and in cross-section in FIG. 2, consists of 1 mil copper conductive film hermetically sandwiched between two 2.5 mil layers of inert polyester substrate (30).

Figure 2:
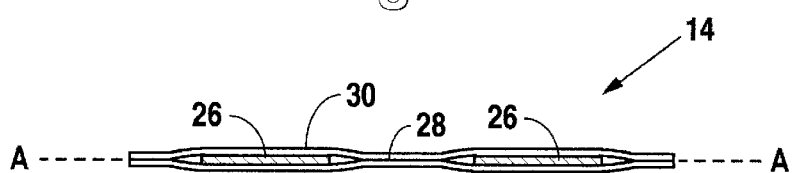
FIG. 2 is a cross-section of the sensing element capacitive array as shown in FIG. 1.
Figure 2A:
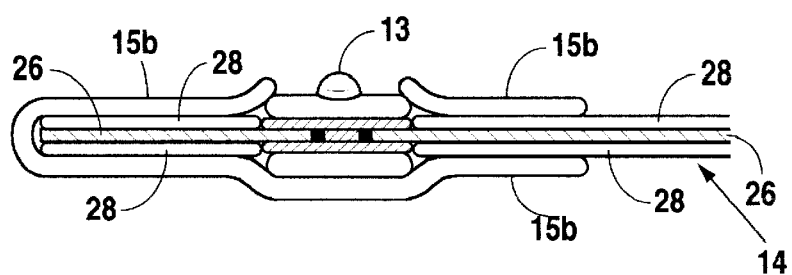
FIG. 2a is a detailed cross-section of a first preferred embodiment of the snap-on connector of the present invention.

Referencing FIG. 2, the cross-sectional structure of sensing element (14) in general, and more specifically, the cross-section located at each connection point (13), is described in more detail. As indicated above, a metallic conductive film, 1 mil thick in the preferred embodiment, serves as capacitive array component (26). Capacitive array component (26) is hermetically sandwiched between two layers of inert polyester substrate (30). Connector (13) is a snap connection of the type that is typically used and referred to as an EKG connector. Attachment of snap connector (13) to conductive film (26) is made first by providing a circular window through polyester substrate (30) of a size sufficient to permit direct contact between the metallic components of snap connector (13) and the metallic conductive film, and then compressing the two-part components of snap connector (13) together so as to penetrate through conductive film (26) and compress a circular portion of conductive film (26) between the electrical contacting elements of snap connector (13). In order to provide further integrity to the connection, the electrical contacting elements of snap connector (13) may be soldered to the copper conductive film (26). Reinforcing layer (15b) is also configured with a window through which the electrically conductive components of snap connector (13) are allowed to protrude. The remaining portion of reinforcing layer (15b) adheres to the outer surfaces and edge of the sandwiched substrate/film/substrate layers as shown. This configuration provides not only an appropriate means for reinforcing the edge of sensing element (14) but also serves to seal the edge and the area around snap connection (13).

Figure 2B:
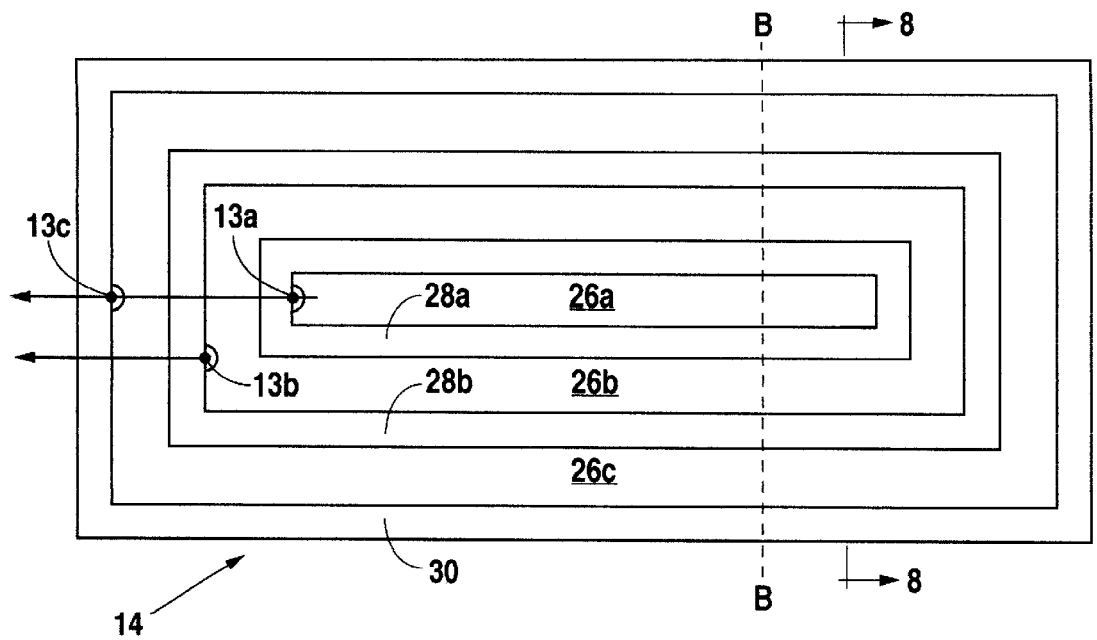
FIG. 2b is a plan view of an alternative sensing element capacitive array utilizing stacked conductive elements within the array.
Figure 2C:
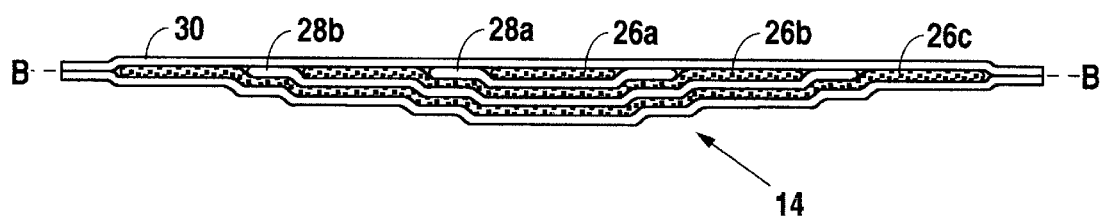
FIG. 2c is a cross-section of the sensing element shown in FIG. 2b taken along line B.

FIGS. 2b and 2c disclose yet another structural arrangement for sensing element (14) that under certain conditions would provide more optimal capacitive characteristics. In FIG. 2b, capacitive array elements (26) are divided into three components (26a, 26b, and 26c) These components are laid one on top of another so that they are concentrically arranged operating a very long interface edge for a relatively small linear geometry. The actual construction of sensor element (14) as described in FIGS. 2b and 2c is best seen in cross-section in FIG. 2c taken along line B in FIG. 2b. While the various array elements (26a–26c) are in fact vertically stacked, the resultant structure is such as to create a sequence of concentric, coplanar elements that function much in the same way as the above-referenced two-dimensional configurations. Interspaces (28a and 28b) in this case would be layers of dielectric material such as, for example, the material utilized for polyester substrate (30). The primary requirement is that these layers be flexible and electrically insulative so as to create the electrical capacitive array described above.

Electrical connections for the embodiment shown in FIGS. 2b and 2c would be made as disclosed at connections (13a, 13b, and 13c). Capacitive elements (26a and 26c) would, in this embodiment, function as a single electrical element of the capacitive array with element (26b) functioning as the opposite element. Connections (13a) through (13c) are made according to this arrangement.

Reference is again made to FIG. 1 for further details on the operation of the electronics of the present invention. As previously stated, when comparator/calibration logic circuit (20) achieves or exceeds a pre-defined high or low ratio limit set by its calibration circuitry in an ongoing manner, its logic circuit will determine whether control monitor module (10) enters a "resting", "monitor", or "alarm" state. Appropriate "hold" and "monitor activate override" commands to the logic circuit may be given by an external operator, such as a patient care giver through appropriate switches integral to the circuitry. Under its own command, the logic circuit will analyze the initial absence of a patient's body mass from sensing element (14) when first activated and will enter a resting or "hold" status. On proximity application of a patient's body mass to sensing element (14) logic circuit (20) will sense the increased capacitance value generated by driver/sensor circuit (18) and enter a "monitor" status mode. On removal of the patient's body mass from sensing element (14) and an equivalent appropriate ratio capacitance value decrease derived from driver/sensor circuit (18), logic circuit (20) will enter an "alarm" status mode. Should this "alarm" status exist for longer than a predetermined, operator programmed time delay, logic circuit (20) will instruct alarm generation circuit (22) to enter an "alarm" mode. The purpose of the operator programmed time delay, if required, is to prevent improper or false alarms being generated by the described device through the transient shifting by the patient of his or her body mass adjacent to sensing element (14). An "alarm" mode activation by control module (10) will trigger activity of nurse call relay circuit (32), which will in turn activate a medical facility's nurse call system (34) if so interfaced.

Should comparator/calibration logic circuit (20) ultimately require alarm generation circuit (22) to enter an alarm generation state caused by the absence of the patient's body mass from the sensing element, the alarm status so generated will be maintained, under normal circumstances, even though the patient reapplies his/her body mass to the sensing element following the generation of such an alarm. Such programming (which may be overridden by the caregiving operator) will dissuade the patient from frequently moving off and on the sensing element. Comparator/calibration logic circuit (20) may also be programmed to perform other functions as required (for instance, automatically shifting to a "monitor" mode from a "resting" or "hold" mode when the patient's body mass has been proximal to sensing element (14) for a defined period of time).

Driver/sensor circuit (18) is positioned in close attachment to sensing element (14) in order to reduce any extraneous electromagnetic field effects. Driver/sensor circuit (18) comprises circuitry appropriate for measuring the capacitance in capacitive array (26) and generating a variable frequency signal relative to the capacitance value. The variable frequency output thus encodes the capacitance value in a signal that is less susceptible to interference from extraneous fields. The signal can be provided through ordinary wire connections (12) in FIG. 1 back to control/monitor module (10).

Reference is now made to FIG. 3 for a detailed description of the structural nature of the system described schematically in FIG. 1. Sensing element (14) is structurally much as described in FIG. 1, being made of a flexible substrate (30) with embedded flexible capacitive array elements (26). Capacitive array (26) is separated by interspace (28). Substrate (30) effectively surrounds and encases capacitive array (26).

At each end of sensing element (14), as shown in FIG. 3 are reinforcing layers (15a) and (15b). These layers, as described generally above with respect to FIG. 2, serve the dual purpose of reinforcing the attachment ends of sensing element (14) and sealing these ends at the same time. At a first end of sensing element (14), reinforcing layer (15a) covers the upper and lower surfaces of sensing element (14) and wraps around its edge much in the manner described in FIG. 2 with respect to reinforcing layer (15b). Hole or slot (11a) is punched through the entire structure (five layers) and is positioned to facilitate the attachment of a means for holding sensing element (14) to the patient's bed.

Likewise, reinforcing layer (15b) is positioned at an opposite end of sensing element (14) and wraps around the edge thereof in the manner described with regard to FIG. 2. Hole or slot (11b) is punched through the layers of sensing mat (14) and provides a means for attaching this end of sensing element (14) to the patient's bed. In addition, hole or slot (11b) provides a strain-relief mechanism as described in more detail below.

Conductors (17a) and (17b) connect the array elements (26) to the electronics of the present invention through connection points (13a) and (13b). As described above, in the preferred embodiment, these connection points (13a) and (13b) constitute EKG-type snap connectors. These type of connectors provide a sufficiently rigid, yet removable electrical attachment. FIG. 3a shows an alternative preferred embodiment and function of hole or slot (11b). To facilitate a strain-relief function on conductors (17a) and (17b), hole or slot (11b) is elongated and provides an aperture through which conductors (17a) and (17b) pass before connecting to connection points (13a) and (13b). In this manner, any strain on conductors (17a) and (17b) pulls at connection points (13a) and (13b) in a direction that is less likely to result in a disconnection.

In the preferred embodiment, driver/sensor circuit (18) is encased within a small enclosure immediately adjacent connection points (13a) and (13b). It is anticipated that in order to minimize external electromagnetic field influences, conductors (17a) and (17b), which are unshielded, would be relatively short. In the preferred embodiment, conductors (17a) and (17b) are approximately 3 inches in length. As indicated and described above, driver/sensor circuit (18) converts the capacitive values measured from sensing element (14) into a frequency output that is less susceptible to external electromagnetic field interference. This frequency signal is provided by way of connector (12) to control monitor module (10) as shown. In the preferred embodiment, connector (12) is a four-conductor telephone-type cable terminating in a removable plug insertable into an appropriate telephone-type jack in control monitor module (10).

In the preferred embodiment, control monitor module (10) comprises a box shell of dimensions approximately 4.50 inches high by 2.25 inches wide by 1.00 inches deep, surrounding the electronics described above. On the external surface of the module enclosure is provided guard (31) which serves the dual purpose of protecting and shielding control button (19) by way of cover panel (33) and acting as an attachment point for the module through strap slots (35). The attachment of monitor module (10) to the patient's bed is described in more detail below.

Control monitor module (10) includes, in the preferred embodiment, a piezoelectric acoustic sounder as is well known in the art for use with alarm systems and the like. Control monitor module (10) of the present invention, however, is structured so as to be capable of incorporating a piezoelectric device much larger than might normally be utilized in a modular enclosure of the size described above. This is possible because the resonance chamber for the piezoelectric sounder is incorporated into the wall structure of the control monitor module box. The cylindrical chamber normally associated with "off-the-shelf" sounders is eliminated and replaced with a chamber created by the front and back walls of the monitor module enclosure. This greatly reduces the amount of space required for a sounder with a high decibel output.

In addition, monitor module (10) retains a plurality of LED indicators as shown to provide the user (the care giver or nurse) with indications regarding the status of the system. According to the functions described above and below, monitor module (10) incorporates low battery indicator (21), check mat indicator (23), alarm indicator (25), monitor mode indicator (27) and hold mode indicator (29).

Monitor module (10) is connected by way of cable (37) to nurse call system connector (43). Connector (43) terminates in a standard phono jack (41) as is typically utilized in existing nurse call system connections. Connector (43) is intended to provide the electrical connection to nurse call system (34) shown above in FIG. 1.

Control monitor module (10) in the preferred embodiment is powered by a 3 VDC power supply typically provided by two AA type alkaline or lithium batteries. The present invention may also operate off of an AC power source with an appropriate AC adaptor circuit. When operable through an AC adaptor, control monitor module (10) incorporates an automatic battery backup switch-over circuit to maintain operation of the device in the event of AC power interruption or failure. Such battery backup systems are well known in the art.

The low battery indicator (21) shown in FIG. 3 is connected to the electronics of the present invention so as to provide two stage indications of the internal power supply. Low battery indicator (21) is configured to begin blinking when the voltage of the internal power supply falls below 2.6 VDC. This would be indicative of a non-urgent need to replace the battery within the unit. A second stage low battery indication provided at LED (21) would occur when the power supply voltage falls below 2.48 VDC, indicating a more urgent need to replace the battery. In conjunction with the blinking low battery LED, an audible signal, as well as a closing (or opening as the case may be) of the nurse call connection would occur.

It should be noted that driver/sensor circuit (18) does not require a separate power supply to convert the capacitance values measured in sensing element (14) to a frequency shift values utilized by control monitor module (10).

Control monitor module (10) is designed to operate through manipulation of a single button to control its mode and status. The LED indicators described above are intended to provide a full system visual status identification and indication means for the user. There are two separate system integrity alarms that are incorporated into the electronics described above. The first involves a disconnected mat state that causes the check mat LED, the alarm, and the nurse call system to activate when the mat is not connected to the system. A second integrity alarm occurs when an internal electronic function failure occurs. When such an internal function failure occurs, all LEDs on control monitor module (10) are illuminated. In addition, the electronics of control monitor module (10) are configured so as to provide a means for indicating the presence of a battery when no LEDs are illuminated. Pushing control button (19) one time will also provide a single, short audible tone to indicate the presence of a battery within the system.

In general, control monitor module (10) is electronically configured to provide multiple alarm tones selectable by the user or installer. Five settings that include a "no audible alarm" state can be controlled and set by a standard DIP switch positioned within the enclosure. These DIP switch settings provide the user with the ability to select the delay time (the time between the sensing of an off-the-mat condition and the initiation of the alarm) and the duration and character of the alarm once it is activated. The electronics are configured so as to permit the selection of instantaneous alarm activation once an off-the-mat condition is detected, in which case, if the patient returns to the mat, the alarm is immediately silenced. Alternatively four or eight second delays between an off-the-mat condition and the alarm can be programmed. When such delays are utilized, it is preferable for the alarm to remain on even after the patient has returned to the mat. Utilization of the externally accessible time delay dip switch settings, as identified above, permit control monitor module (10) to conveniently and concurrently perform the dual roles of bed monitor or chair monitor as required.

In addition, the dip switches available to the user permit modification of a number of additional settings associated with the alarm and the type of system control monitor module (10) is utilized in conjunction with. The dip switches permit the selection of four different alarm tones for a particular control monitor module (10) so as to permit a care giver to distinguish between various patients within a single room or otherwise identify a particular patient by a particular type of alarm tone.

The dip switch settings also permit the user to time out the alarm tones for either a 30 second or two minute period of time. The switches also permit the user to select a completely silent alarm at the control monitor module while still utilizing and activating the existing nurse call system. Finally, the dip switches permit the system of the present invention to adapt to a normally open or a normally closed nurse call system, both of which are known in the art. These user accessible dip switch settings permit the system of the present invention, and in particular the control monitor module (10) of the system to be readily adaptable to any of a number of existing systems and environments within which the patient monitor is utilized.

The process of installing and activating the system shown in FIG. 3 is simple and straightforward. With the appropriate batteries installed and the connections between control monitor module (10) and driver sensor circuitry (18) in place, connections are made at (13a) and (13b) to sensing element (14). Three audible pulses are heard to indicate that the system has been switched on when this mat connection is made. Likewise, when this mat connection is removed, a single audible pulse indicates the system is off. Should control monitor module (10) be connected in like manner to a pressure sensitive switch array mat, two audible pulses are triggered. Control monitor module (10) then automatically continues to function in conjunction with the pressure sensitive mat with no external adjustment to its circuitry, in a manner identical to its function with the dielectric shift sensing mat of the present invention.

In the activation process, LED indicators on the front panel flash once to indicate their function and then the single LED hold indicator (29) activates. Once a patient is placed on the mat, the system will automatically enter a monitor mode after 15 seconds. Monitor mode may alternatively be immediately activated by pushing control button (19). The system may be switched back and forth between the hold and monitor mode by repeatedly pushing control button (19). It should be noted that the automatic activation of a monitor mode after 15 seconds, once a patient's body mass has been applied proximal to the sensing mat is different from earlier described and utilized circuits. In the present invention, the patient's body mass does not have to be removed from the sensing mat and subsequently returned to the sensing mat to reactivate the automatic monitor mode from the hold mode, once the hold mode has been manually activated. As long as the patient's body mass is consistently in contact with the sensing mat, the system will automatically enter the monitoring mode after 15 seconds with no necessity to remove the patient's body mass from the sensing mat and then reapply it.

It is anticipated that the system of the present invention can be installed with the elements shown in FIG. 3 or may be installed in conjunction with an existing nurse call activation system within the hospital. The switches within monitor control module (10) allow it to activate either a normally open or normally closed nurse call switch system.

Reference is now made to FIG. 4 for a detailed description of the placement of the apparatus of the present invention on the typical hospital bed. Bed (39) incorporates a plurality of side rails (38) that facilitate both the attachment and the use of the system of the present invention. Patient (40) is positioned on bed (39) as shown. As described above, the placement of sensing element (14) of the present invention is best made near the larger mass areas of patient (40). In FIG. 4, sensing element (14) is positioned beneath the upper torso portion of patient (40). Sensing element (14) is placed beneath a mattress sheet or mattress cover (not shown) in an area beneath the upper torso of patient (40). Sensing element (14) is positioned on and held to the mattress of bed (39) through the use of elastic straps (9a) and (9b) as shown. In an alternative embodiment, a reverse side of sensing element (14) may be provided with adhesive material that allows the removable positioning of sensing element (14) on mattress (39) without permanent attachment to its surface. Various adhesives are well known in the art to permit such removable attachment of a flexible surface.

Positioned immediately adjacent to sensing element (14) is driver/sensor circuit (18). In the preferred embodiment both the enclosure and the circuitry associated with driver/ sensor circuit (18) are sufficiently lightweight and flexible as to easily be suspended by connectors (17a) and (17b) along the side of mattress (39). It is anticipated that the mattress cover or mattress sheets (not shown) would partially cover driver/sensor circuit enclosure (18). Conductor (12) connects driver/sensor circuit (18) to control monitor module (10) which is more rigidly mounted at a position near the patient on the structural components of bed (39) or on the wall adjacent to the head of the patient's bed. Attachment to the wall is effected through the use of a wall mounted bracket that appropriately engages and retains strap slots (35).

Various mechanisms for the positioning and placement of control monitor module (10) are disclosed in FIG. 5, FIG. 6, and FIG. 7. FIG. 5 discloses the manner in which control module (10) may be mounted on a patient's wheelchair through the use of mounting clip (70). The longer section (72) of wheelchair mounting clip (70) is slid over the flexible seat backing typically found on a patient's wheelchair, with the longer section (72) of wheelchair mounting clip (70) facing towards the front of the chair. Wheelchair mounting clip (70) is positioned in this manner close to one of the wheelchair handles. Control module (10) is then mounted on the shorter hook side (74) of wheelchair mounting clip (70) by inserting hook element (76) through lower strap slot (35) of control unit finger guard (31).

In the preferred embodiment, control monitor module (10) is attached to the wall adjacent to the patient's bed (39) by means of wall clip (80), shown in FIG. 6, which in turn has been attached to the wall structure through the use of either screws, positioned through holes (88) in back plate (82), or through the use of double sided adhesive tape placed on the back of back plate (82). Front lip (86) of hook structure (84) protruding from clip (80) engages through top strap slot (35) of finger guard (31) to secure control monitor module (10) to the wall.

Yet a further, more secure, means for attaching control monitor module (10) to a wall adjacent the patient's bed is disclosed in FIG. 7. Lockable wall clip (90) is attached to the wall surface in much the same manner as described above with respect to wall clip (80) shown in FIG. 6. Lockable wall clip (90) is attached to the wall structure through the use of either screws, positioned through holes (98) in back plate (92), or through the use of double sided adhesive tape placed on the back of back plate (92). Protruding from back plate (92) of clip (90) is support plate (94) with extended edge (96) through which is positioned hole (99). Extended edge (96) of support plate (94) engages through top strap slot (35) of finger guard (31) to secure control monitor module (10). In this manner, hole (99) aligns with hole (97) positioned in cover panel (33) and permits the insertion of locking device (95) therethrough. Locking device (95) may be any of a number of well known devices designed to secure two objects through aligned holes. Small pad locks and plastic cable ties are typical examples.

An alternative method of positioning control monitor (10) adjacent to a patient's bed (39) is by attaching it to bed railing (38) by means of flexible attachment strap (7). Attachment strap (7) slips through strap slots (35) (shown in FIG. 3) and attaches control monitor module (10) to the bed in a position serviceable by care giver personnel. It is anticipated that the care giver would be the individual responsible for activating and monitoring the function of the system of the present invention so control monitor module (10) is positioned on the outside of bed rail (38). Finally, as described above, connector (37), which may be an electrical cord of any reasonable length, connects the system of the present invention to existing nurse call system connections. In the preferred embodiment, connecting cord (37) is completely detachable from control monitor module (10) through the use of any suitable, easy to use electrical connector (such as a modular U.S. style telephone connector) this enables connecting cord (37) to be completely removed from control monitor module (10) when such monitor module may be utilized as a mobile monitor—for instance on a patient's wheelchair—and where no connection is required between control monitor module (10) and a nurse call system connection.

It is anticipated that the flexible structure of the sensing element of the present invention permits large variations in the placement for association with a particular patient. The adaptability of the electronics of the system further permits use of a single sensing element structure in a number of applications with variations in the patient body mass that is brought in proximity to the sensing element.

In addition to being installed in environments where patient monitoring systems have not been in use, the structures of the present invention lend themselves to be retrofit into existing patient monitor systems previously based upon alternate sensing mechanisms. In many cases, existing electronics are already in place that provide the link between the patient monitor and the nurse's call system.

OPTIONAL SYSTEM COMPONENTS

One objective of the present invention is versatility of use in conjunction with a number of different nurse call systems installed within a number of different health care environments. FIGS. 8 through 15 provide various additional optional elements to the patient monitoring system that have specific advantages under certain conditions and patient environments. The objective of versatility is achieved through the consistent use of 4 and 6 wire modular phone jack connectors and the use of "pass-through" electronics that permit the devices to be "daisy chained" together into the system.

Figure 8:
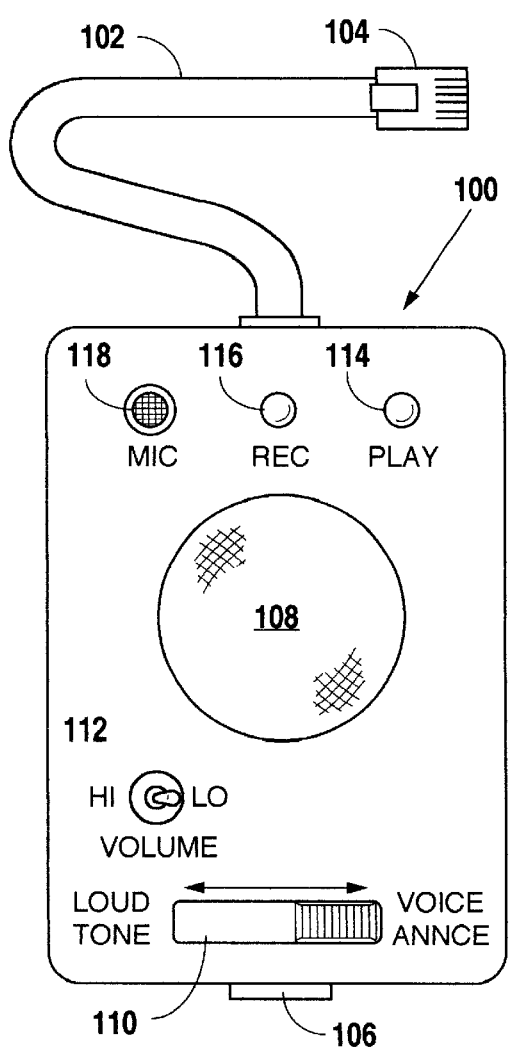
FIG. 8 is a plan view of the in-line auxiliary alarm module of the present invention.

FIG. 8 is a plan view of an auxiliary alarm module (100) of the present patient monitoring system. Alarm module (100) incorporates means for providing specialized alarms in the vicinity of the patient as conditions might require. Module (100) provides (in addition to the alarm in the control monitor module (10) and the standard nurse call system alarm) a selectable extra loud tone or a voice announcement alarm. Module (100) is connected to the nurse call system output of control monitor module (10) of the present invention by way of 6 wire modular cord (102) and modular phone jack (104). Connection to the existing nurse call system is maintained through 6 pin modular output connector (106) in a manner described in more detail below.

Utilizing well known electronic circuits, module (100) provides the ability to switch between an extra loud tone and a voice announcement by way of switch (110). Both audible alarms are produced through speaker (108) positioned centrally in module (100). In either case the volume of the audible alarm selected may be incrementally varied between high and low levels through the use of volume switch (112). The extra loud tone generated as an alarm in module (100) is electronically established through well known tone generating circuits triggered by an alarm state as described in more detail below. The voice announcement alarm is likewise triggered by an alarm state as relayed by control monitor module (10) and provides a digitally recorded voice message appropriate for the particular patient's situation. Commands such as "please return to bed" may be digitally recorded to be played back upon the occurrence of an alarm event. To facilitate the recording of such customized commands, module (100) provides a play button switch (114), a record button switch (116), and a microphone (118). The electronic circuits for providing these functions are well known in the art and may typically be found in hand held digital voice memo recorders and telephone answering machines and the like.

Figure 9:
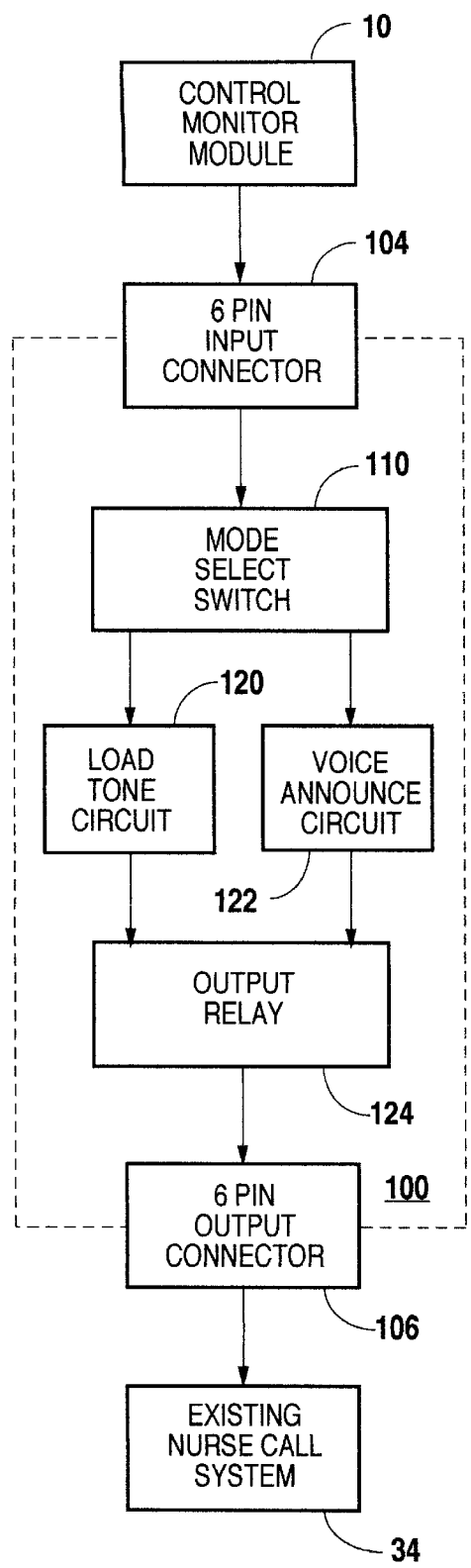
FIG. 9 is a schematic block diagram of the functional elements of the in-line auxiliary alarm module shown in FIG. 8.

Reference is now made to FIG. 9 for a general description of the various electronic circuit components that are incorporated into auxiliary alarm module (100). As indicated above, control monitor module (10) provides, by way of its output to the nurse call system, a switched indication of an alarm state. This is received into module (100) through 6 pin input connector (104). Depending on the position of mode select switch (110), the alarm condition trigger is provided either to loud tone circuit (120) or voice announce circuit (122). Whichever circuit is activated, the audible alarm is generated through the speaker (108) of module (100). In conjunction with generating the audible alarm, both loud tone circuit (120) and voice announce circuit (122) activate output relay (124) which duplicates the on-off state of the alarm condition provided by control monitor module (10). This on-off alarm condition state is output from module (100) through 6 pin output connector (106) where the system is again connected to the existing nurse call system as described above with the primary embodiment.

Figure 10:
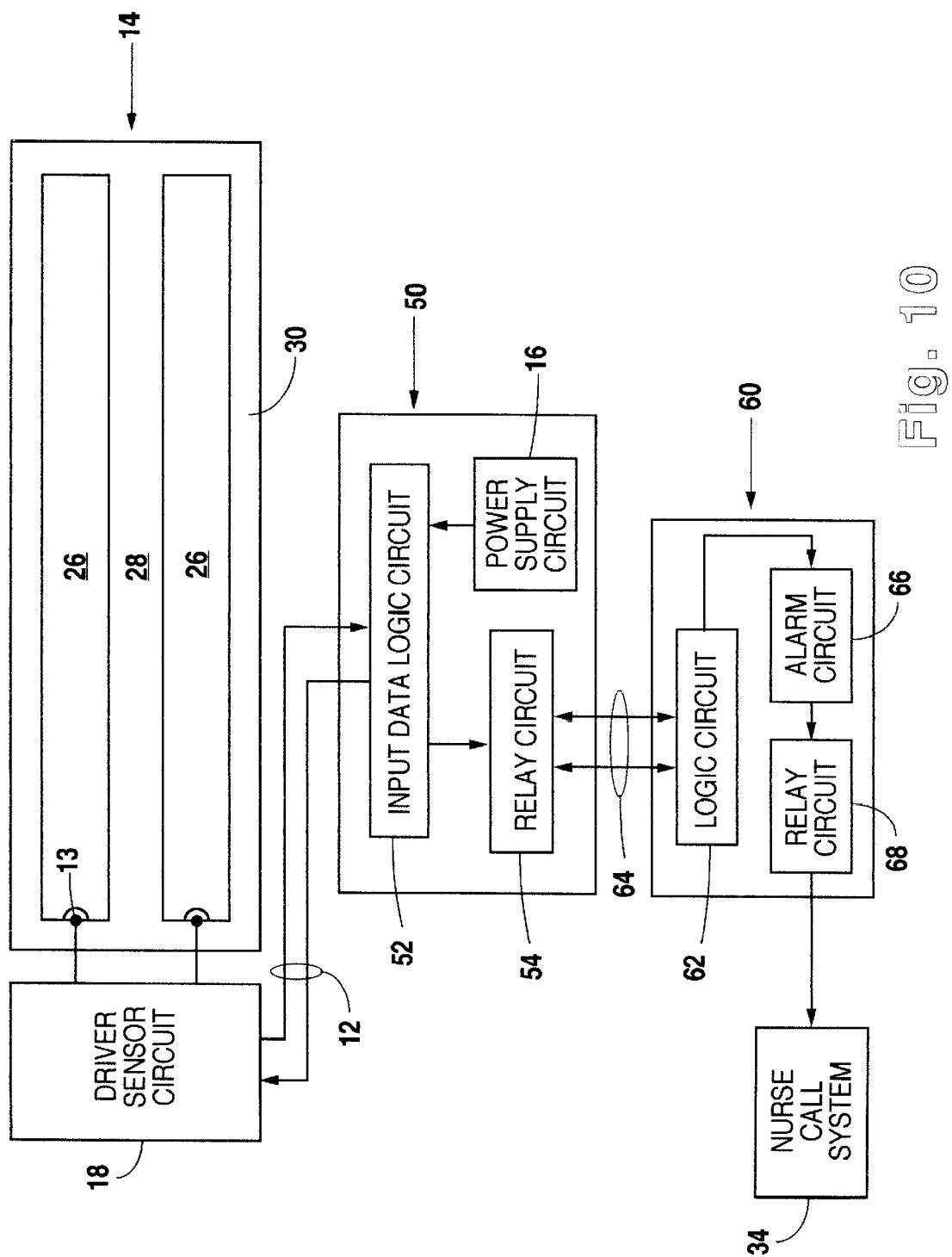
FIG. 10 is a schematic block diagram of a second preferred embodiment of the system of the present invention.

In addition to being installed in environments where patient monitoring systems have not been in use, the structures of the present invention lend themselves to be retrofit into existing patient monitor systems previously based upon alternate sensing mechanisms. In many cases, existing electronics are already in place that provide the link between the patient monitor and the nurse's call system. FIG. 10 describes just such a situation and indicates how the structures of the present invention can be retrofit to take advantage of the existing electronics in place and still provide the benefits of the improvements found in the present invention.

In place of control module (10) in the above described embodiment of the invention, interconnect adaptor module (50) connects with driver/sensor circuit (18). The structures of sensing element (14) and its capacitive array (26) with interspace (28) positioned within substrate (30) are basically as described above. Within interconnect adaptor module (50) is input data logic circuit (52) which in turn is connected with relay circuit (54). Both are provided with power from power supply circuit (16). Power supply circuit (16) also supplies power through interconnection (12) to driver sensor circuit (18).

Interconnect adaptor module (50) is connected to an existing switch-based monitor/control unit (60) through logic circuit (62) contained therein. Connection (64) therefor typically carries an on/off condition between interconnect adaptor module (50) and existing switch based monitor/control unit (60). Logic circuit (62) of switch based monitor/control unit (60) typically generates an electrical signal into connections (64) which, if the system were using a mechanical switch sensor would determine the opening or closing of contacts within that sensor. The driver current produced by logic circuit (62) might typically be 6–10 volts at 2–3 microamps. Should the contacts of a mechanical switch sensor be closed, thereby completing the driver circuit, logic circuit (62) of the switch based monitor\control unit (60) would signal and indicate a monitoring status mode within monitor/control unit (60). Should the switch sensor contacts open in such an arrangement, then by sensing an open circuit status, logic circuit (62) would in turn generate an appropriate status signal which would activate alarm circuit (66) and relay circuit (68) to effectively generate an alarm condition from monitor/control unit (60). This alarm status condition may or may not be interconnected with the medical facility's nearest call system as desired.

The principle effect of the described interconnect adaptor module (50) is to replace, in an electrically transparent manner, the contact points of a mechanical switch sensor with those of an appropriate relay circuit (most preferably of a solid state design) which will effectively imitate the mechanical switch sensor from the viewpoint of monitor/control unit (60). A capacitance shift value produced by sensing element (14), which might typically be 20 picofarads in a resting, unoccupied state, to 200 picofarads or more in an active occupied state is converted by driver/sensor circuit (18) to an equivalent frequency drop generated by an appropriate oscillator circuit imbedded in driver/sensor circuit (18). This oscillator driven frequency drop may typically be 100 kilocycles in a resting unoccupied state to 20 kilocycles in an active occupied state. This frequency shift signal is carried through conductive elements (12) from driver/sensor circuit (18) to input data logic circuit (52) within interconnect adaptor module (50). By analyzing this input frequency shift, the input data logic circuit (52) may determine the active/occupied status or equivalent inactive/unoccupied status of capacitive sensing element (14). This data is fed into relay circuit (54), also contained within interconnect adaptor module (50, which will open or close its secondary conducting elements interfacing directly to logic circuit (62) of monitor control unit (60). In this manner, the alternative manufacturer's monitor control unit (60) may, through interconnect adaptor module (50) and driver/sensor circuit (18) directly interface, and equivalently and appropriately respond to status signals generated by the capacitive sensing elements of the present invention.

Those skilled in the art will also recognize that appropriate adaptor circuit modules could be incorporated in line with the patient monitoring system of the present invention in order to allow the use of switch based sensor mats in conjunction with the control monitor module (10) based system of the first preferred embodiment. Such a switch to capacitance adaptor circuit would receive the on/off input from a pressure sensing mat (for example) by sampling the open or closed status of the switching circuit at a preset sampling weight (for example, four samples per second). Appropriate, well known, circuit elements would respond to the on/off condition of the pressure sensing mat by generating a capacitance value at an output connection in one of two capacitance ranges. In the preferred embodiment, for example, a switch off condition in the pressure sensing mat could originate a 10 to 20 picofarad capacitance value at the connector output. Likewise, a switch on condition in the pressure sensing mat would generate a 750 to 1000 picofarad capacitance value. These capacitance values would be seen by the driver/sensor circuit of the present system and would be appropriately interpreted into a frequency signal for the control monitor module.

In similar fashion, appropriate circuits, well known in the art, could be inserted between other manufacturer's capacitance based sensing mats in order to bring the capacitance ranges for alarm conditions into line with the system of the present invention. As an example, an input capacitance value of 10 to 20 picofarads could translate directly to the same output capacitance range while an input capacitance range of 200 to 400 picofarads (would be translated to an output capacitance range of 750 to 1000 picofarads in order to match with the parameters of the system of the present invention).

Figure 11A:
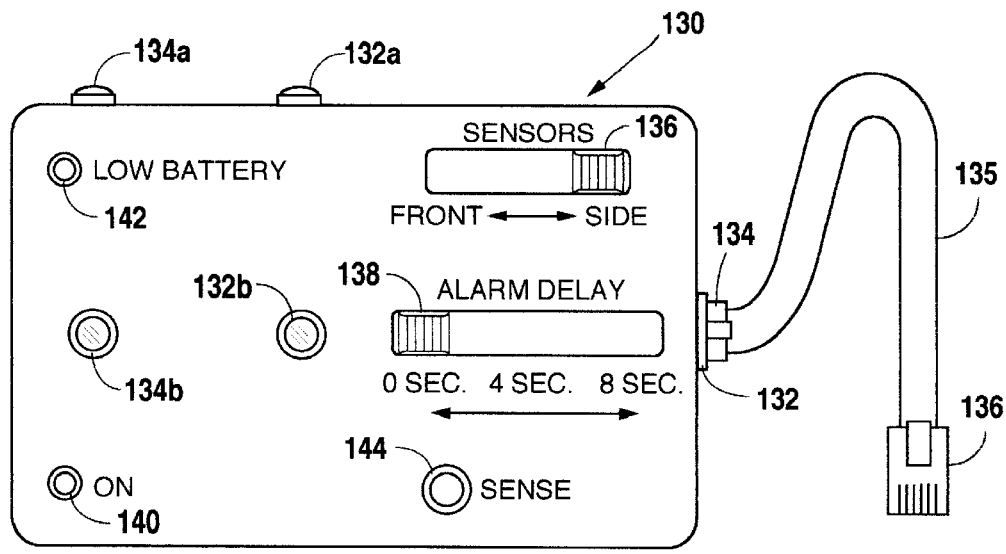
FIG. 11a is a plan view of the active infra-red sensing module of the present invention.
Figure 11B:
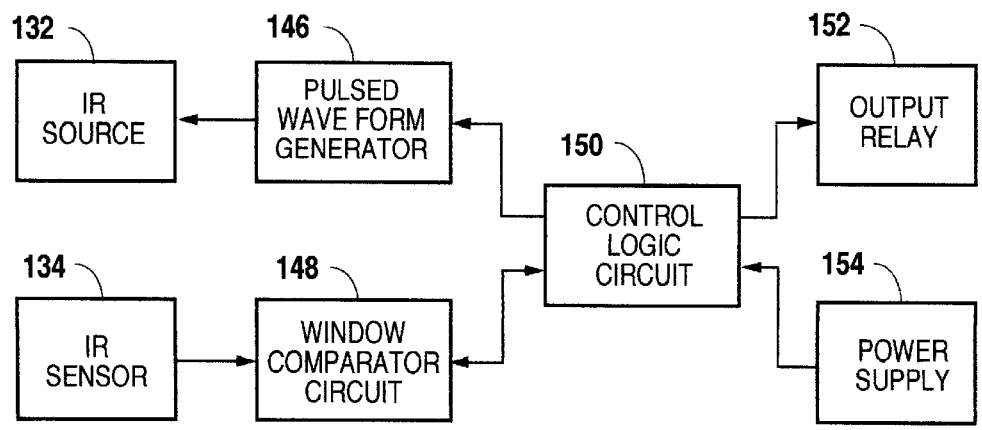
FIG. 11b is a schematic block diagram of the functional elements of the active infra-red sensing module of the present invention.

FIG. 11a and FIG. 11b provide an optional mechanism for sensing the presence or absence of a patient within a predefined space such as a hospital bed, a wheel chair, or a hospital room toilet facility. The device disclosed comprises the use of a reflective energy beam such as is described in U.S. Pat. No. 5,471,198 entitled Device for Monitoring the Presence of a Person Using a Reflective Energy Beam, the disclosure of which is incorporated herein by reference. In the preferred embodiment an infrared (IR) sensor system is employed. Active IR sensing module (130) is designed to replace the capacitive sensor mat (14) described above. Otherwise the system components required for patient monitoring are the same as described above. Module (130) is connected to control monitor module (10) sensor input by way of modular cord (135) with terminal modular connectors (136) and (134). Modular connector (134) is plugged into modular jack (133) positioned on sensor module (130).

IR sensor module (130) incorporates bi-directional IR transmitters (132a)/(132b) and sensors (134a)/(134b) switchable by means of directional slide switch (136). In this manner the most appropriate orientation and attachment of module (130) can be achieved. In either case, electromagnetic waves are generated by IR transmitters (132a)/(132b), reflect off of objects (the patient) within the field of view, and are detected by IR sensors (134a)/(134b). In the preferred embodiment a selectable alarm delay time is provided to avoid false alarms for ordinary patient movement. This alarm delay selectability is provided by way of three position slide switch (138). Module (130) additionally provides an on indicator (140) and a low battery indicator (142). A sense indicator (144) is illuminated when an occupant is detected within the field of view.

FIG. 11b describes the basic functional circuit elements provided in sensor module (130) to achieve the operation as discussed above. Control logic circuit (150), which in the preferred embodiment is a digital processor controls pulsed waveform generator (146) which in turn controls IR source (132) which generates the interrogating energy beam. The reflected beam is received back at IR sensor (134) whose output passes through a window comparator circuit (148) tuned to identify appropriate variations in the reflected signal indicative of an alarm or a no-alarm condition. When an alarm condition is detected due to the movement of a patient from the field of view for a selectable period of time (0 seconds, 4 seconds, or 8 seconds) control logic circuit (150) activates output relay (152) which provides the preferred on-off alarm condition described above in conjunction with the first preferred embodiments of the present invention. The sensor module (130) retains its own internal power source (154) as indicated and is powered on when this power source (battery) is installed. The sensor module (130) described is operable in three modes once powered. A first, passive, "hold" mode represents a standby condition prior to the sensing of an occupant in the field of view for the sensor. A second, "sense" mode represents the condition where an occupant has been sensed within the field of view and the sense indicator (144) is illuminated. The third, "alarm" mode occurs when the occupant leaves the field of view for at least a selectable period of time (the alarm delay). Under "alarm" conditions, an internal relay (152) is closed for ten seconds (an alarm condition that is output to the control monitor module) before returning to the "hold" mode.

Figure 12:
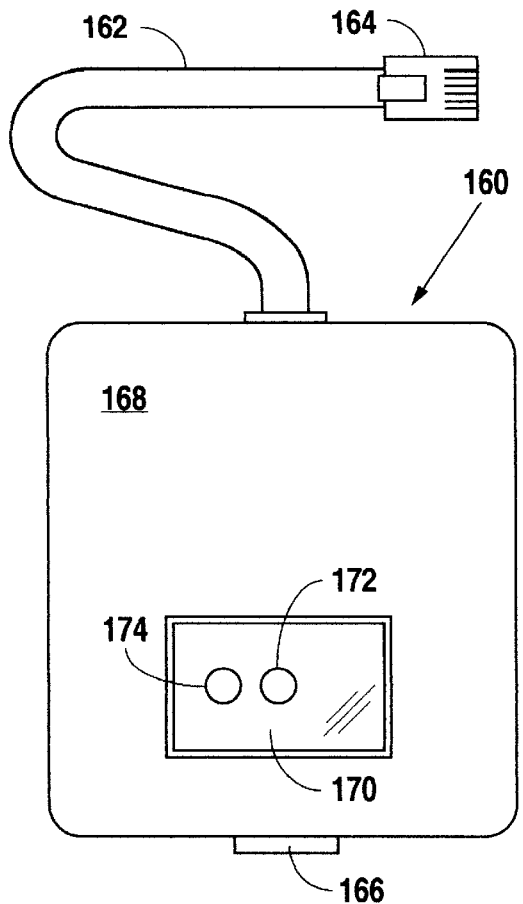
FIG. 12 is a plan view of the in-line elapsed time module of the present invention.
Figure 13:
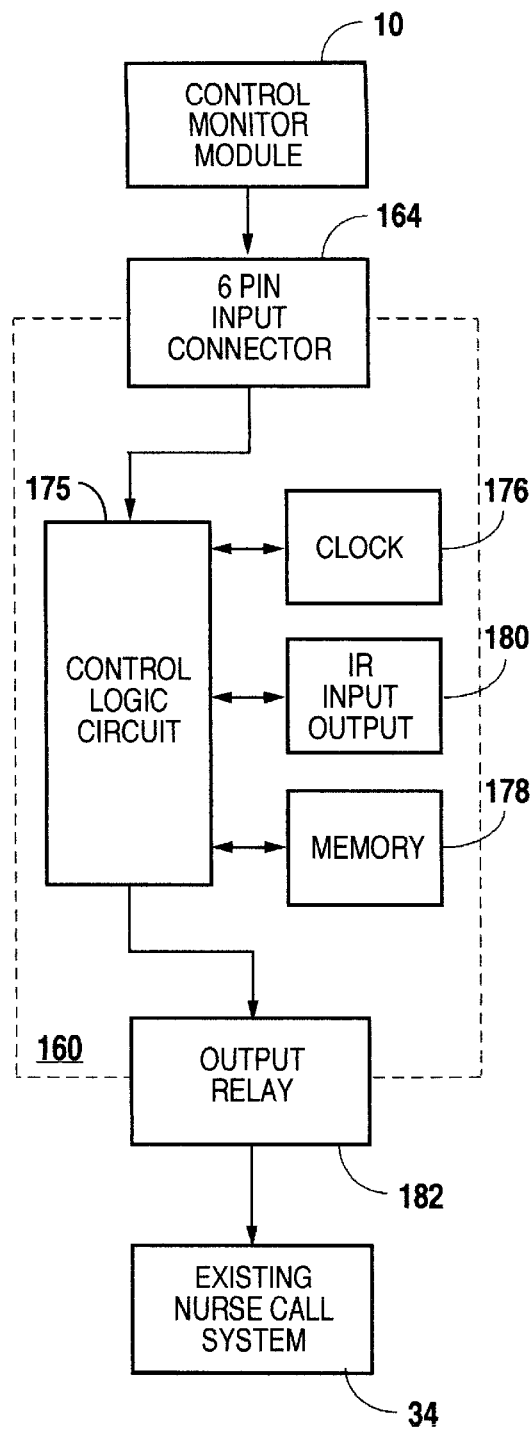
FIG. 13 is a schematic block diagram of the functional elements of the in-line elapsed time module of the present invention.

FIGS. 12 and 13 disclose a further optional, in-line component of the patient monitoring system of the present invention designed to provide a record of alarm events and care giver response times. Elapsed time module (160), like auxiliary alarm module (100) described above, may be inserted into the system in-line between the control monitor module and the existing nurse call system. Elapsed time module (160) comprises modular cord (162) terminating in modular phone jack (164) for connection to control monitor module (10), or to a device such as auxiliary alarm module (100) which is connected to control monitor module (10).

Externally, module (160) is a simple device that is positioned in-line in the system, having output modular connector (166) for further connection of the existing nurse call system. On front panel (168) of module (160) is positioned IR window (170) which is transparent to IR transmitter (172) and IR sensor (174). This transmitter/sensor pair carries out data communication between module (160) and an external, IR communication capable, programmable processor. The function of elapsed time module (160) is understood from the schematic block diagram shown in FIG. 13. Module (160) includes control logic circuit (175), which in the preferred embodiment is a digital microprocessor. Control logic circuit (175) receives the on-off alarm status of the overall system as communicated by control monitor module (10) through 6 pin input connector (164). Control logic circuit (175) functions in association with clock (176) as an event recorder by storing in memory (178) an array of event data comprising alarm state and time every time the alarm condition switches state. Thus, when an alarm condition is triggered control logic circuit (175) stores the date/time of the event and waits for the next change in alarm status, which will most likely be the deactivation of the alarm by the responding care giver. In this manner a record of patient movement and care giver response is maintained.

In the preferred embodiment, module (160) is provided with memory sufficient to maintain a record of 100 events. IR input/output (180) is provided to communicate or download this data from module (160) to a data processing device for reporting and analysis. In addition, the clock parameters may be set and reset through this same IR communication link. The circuitry and protocols by which this communication may be carried out are well known in the art and are now commonly used in conjunction with various data processing and data storage devices. As indicated above, elapsed time module (160) is an in-line device that duplicates the input alarm on-off state at an output relay (182) that provides this alarm state through 6 pin output connector (166) to the existing nurse call system (34).

Figure 14:
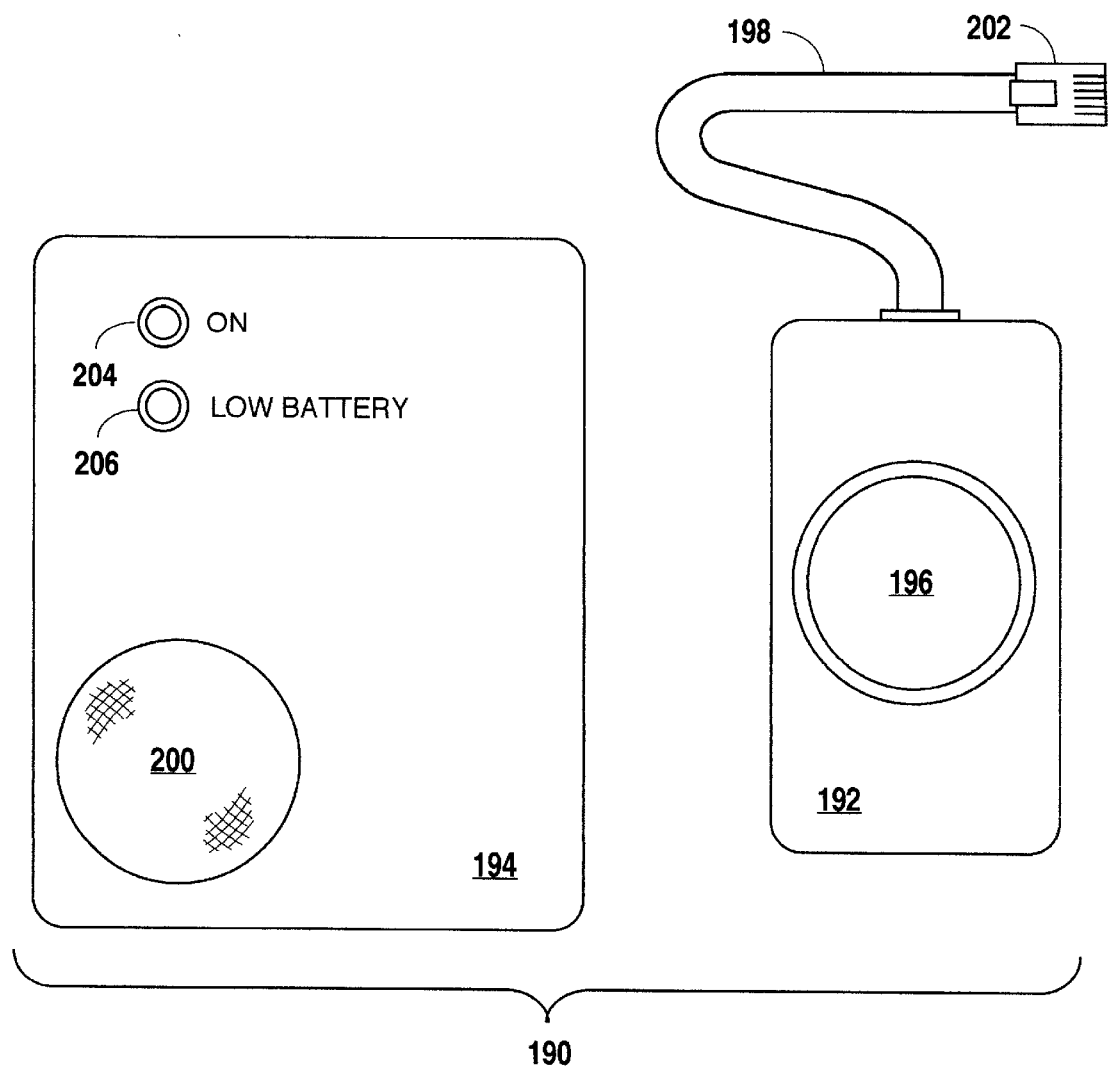
FIG. 14 is a plan view of the wireless transmission modules of the system of the present invention.
Figure 15:
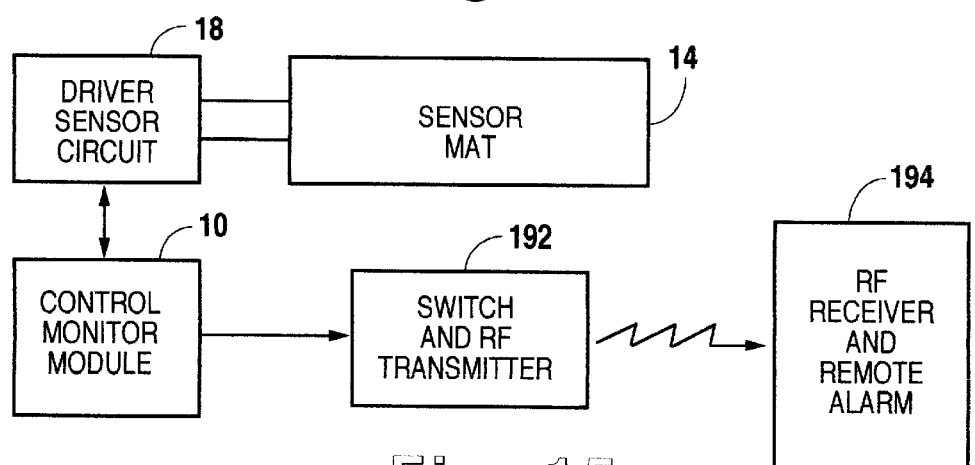
FIG. 15 is a schematic block diagram of the system of the present invention incorporating the wireless transmission modules shown in FIG. 14.

FIGS. 14 and 15 describe yet another optional component operable in conjunction with the system of the present invention. Wireless remote alarm module (190) comprises two primary elements; wireless transmitter (192) and wireless receiver (194). Wireless module (190) is designed to function in the absence of an existing nurse call system, a condition that might be found for example within a residential home environment. In addition (or in place of) the alarm provided by the control monitor module (10) or the auxiliary alarm module (100), wireless module (190) provides a remote alarm activated by the sensor systems described above. The combination of wireless transmitter (192) and wireless receiver (194) is frequently utilized in the art as a wireless doorbell system or the like. Such radio frequency transmitters and receivers are capable of operating over short distances and provide a convenient means for signalling events within a residential dwelling. Transmitter (192) is connected to the system of the present invention in place of the existing nurse call system through modular cord (198) terminating in modular phone jack (202). One manner of operating transmitter (192) is by pushing button switch (196) in the manner typical for such signalling systems. A second manner of activating transmitter (192) is by using the on-off alarm state provided by the control monitor module (10) which is connected in parallel with switch (196) within transmitter (192). In either case, transmitter (192) generates a radio frequency signal that is readily detectable by wireless receiver (194). Receiver (194) is a self-powered RF tuned receiver that incorporates an alarm (or signal) relay which generates an alarm tone though speaker (200). System on and low battery indicators (204) and (206) are provided. In this manner, the remote alarm will be activated if either the patient signals the care giver by pressing button switch (196) on transmitter (192) or the control monitor module (10), in response to a condition from a sensor device, indicates an alarm on state in the system. A typical arrangement according to this function is shown in FIG. 15 wherein sensor mat (14), connected through driver sensor circuit (18) provides the patient occupancy state to control monitor module (10), which in turn relays this state to RF transmitter (192). Transmitter (192) operates as described above to send a signal to receiver (194) to alert the remote care giver of the alarm condition.

Figure 16:
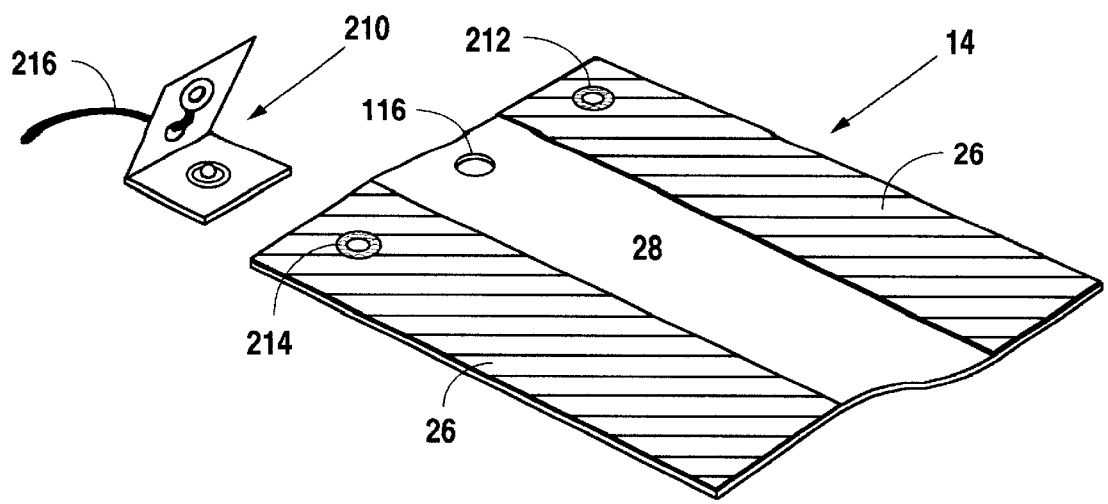
FIG. 16 is an exploded perspective view of an alternative attachment mechanism for the snap-on electrical connectors of the system of the present invention.
Figure 17A:
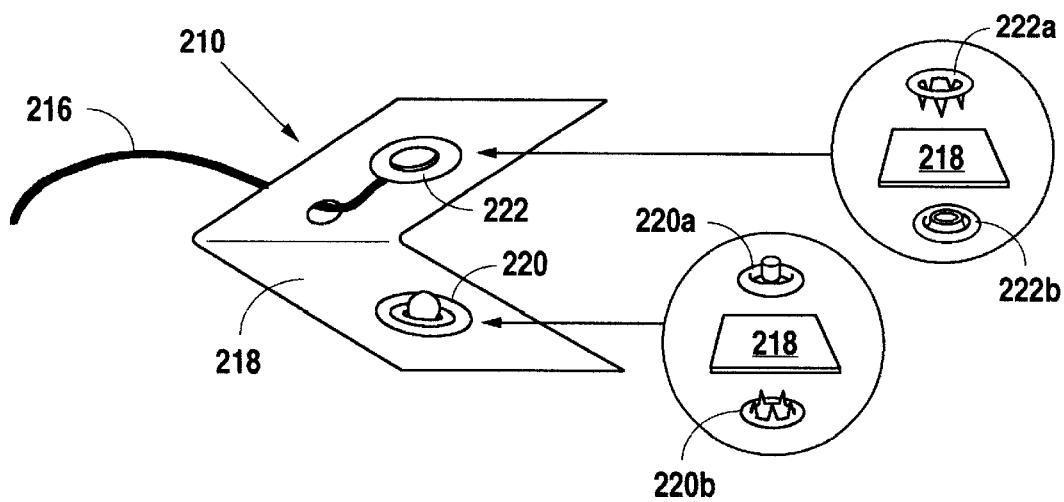
FIG. 17a is a detailed exploded perspective view of the snap-on connectors shown in FIG. 16.
Figure 17B:
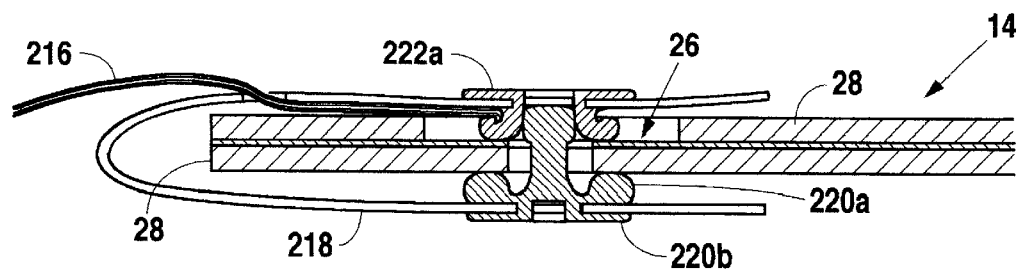
FIG. 17b is a detailed cross-sectional view of the snap-on connectors shown in FIG. 16.

Reference is now made to FIG. 16, FIG. 17a, and FIG. 17b for a description of an alternative mechanism for attaching conductors to the capacitance sensing mat of the present invention. FIG. 16 shows one end of sensing element (14) with connection points (212) and (214) appropriately positioned on capacitive array components (26). In the alternative embodiment described herein, connection points (212) and (214) are apertures cut into sensing element (14) for attachment of snap-on connector (210). Conductor (216) provides the electrical connection from snap-on connector (210) to the balance of the electronics of the system of the present invention. Connection points (212) and (214) each comprise holes or apertures through the layers of sensing element (14) as well as a concentric window through the upper layer of insulation on sensing element (14) through to the conductive components (26).

Reference is now made to FIG. 17a for a detailed description of the structure of snap-on connector (210) as used in FIG. 16 above. Snap-on connector (210) is comprised of female snap component (222) and male snap component (220). Each of these snap components are positioned on flexible support structure (218). Support structure (218) is folded as indicated to permit female snap component (222) to mate with male snap component (220). The detailed structures of the snap components and their assembly is also disclosed in FIG. 17a as is well known in the art.

FIG. 17b shows in cross-sectional view the attachment of snap component (210) to sensing element (14) to provide electrical connection thereto. Sensing element (14) is shown in its multi-layer configuration comprising substrate layers (28) and conductive layer (26). Flexible support structure (218) retains and appropriately positions male snap component (220) below sensing element (14) and female snap component (222) coaxially above sensing element (14). In this manner snapping the components together creates pressure against conductive layer (26) through the window aperture described above in the upper substrate layer (28). Electrical connections provided by way of wire conductor (216) as described above.

Figure 18:
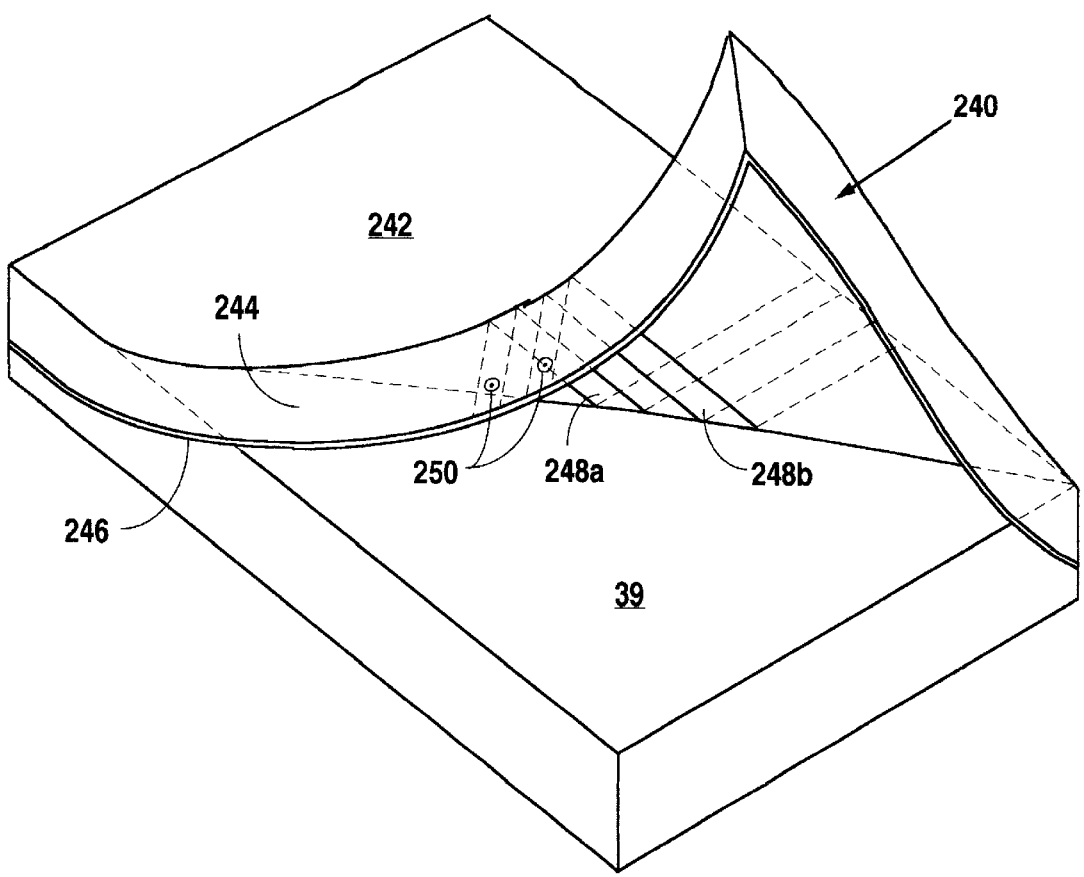
FIG. 18 is a perspective view of an alternative mattress cover embodiment of the present invention.
Figure 19:
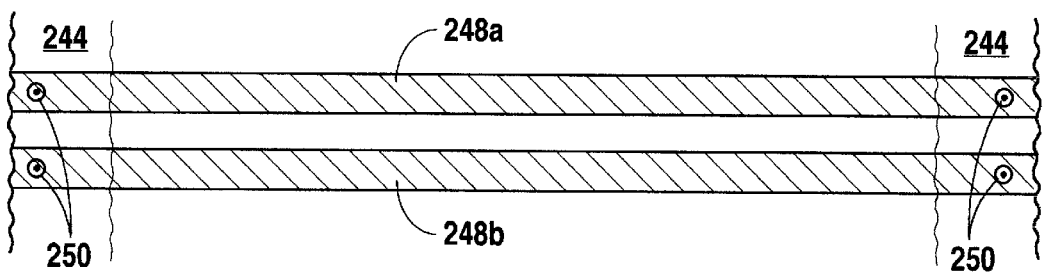
FIG. 19 is a detailed plan view of the underside of the mattress cover embodiment shown in FIG. 18.

Reference is now made to FIGS. 18 and 19 for a further alternative embodiment of the sensor structure of the present invention. FIG. 18 discloses in perspective view the implementation of the capacitive sensing elements of the present invention on the underside of a typical bed mattress cover. In this manner the sensing element component of the present invention is semi-permanently established on the patient's bed in a manner that eliminates the need to replace sensing elements after use. In the embodiment described herein, bed (39) is covered with mattress cover (240) having a generally planar top surface (242) surrounded by orthogonal wall components (244). As is typical in the art, an elastic band (246) is placed on the periphery of wall components (244) in order to secure the mattress cover to the surface of bed The capacitive sensing array in this embodiment comprises a pair of bands (248a) and (248b) made up of principal conductive ink deposited on an underside of mattress cover (240) as shown. Various durable conductive materials may be utilized for the deposited capacitive sensing array elements. Appropriate snap connectors (250) are positioned at terminal ends of each conductive band (248a) and (248b) as in a manner similar to that described above in conjunction with the disposable sensing element. In this manner electrical connections can be made to the under mattress cover sensing element at the side of the bed where wall panels (244) of mattress cover (240) extend down.

In FIG. 19 a more complete view of the printed conductive ink sensing elements (248a) and (248b) are shown. In this view the underside of top panel (242) of mattress cover (240) is shown flattened out. Side wall panels (244) are shown on either side bearing the terminal ends of conductive bands (248a) and (248b). Positioned at these terminal ends just inside of elastic band (246) are connectors (250) positioned as described above. The balance of the components of the present invention may be utilized in conjunction with the under mattress cover sensing element of this alternative embodiment.

Figure 20:
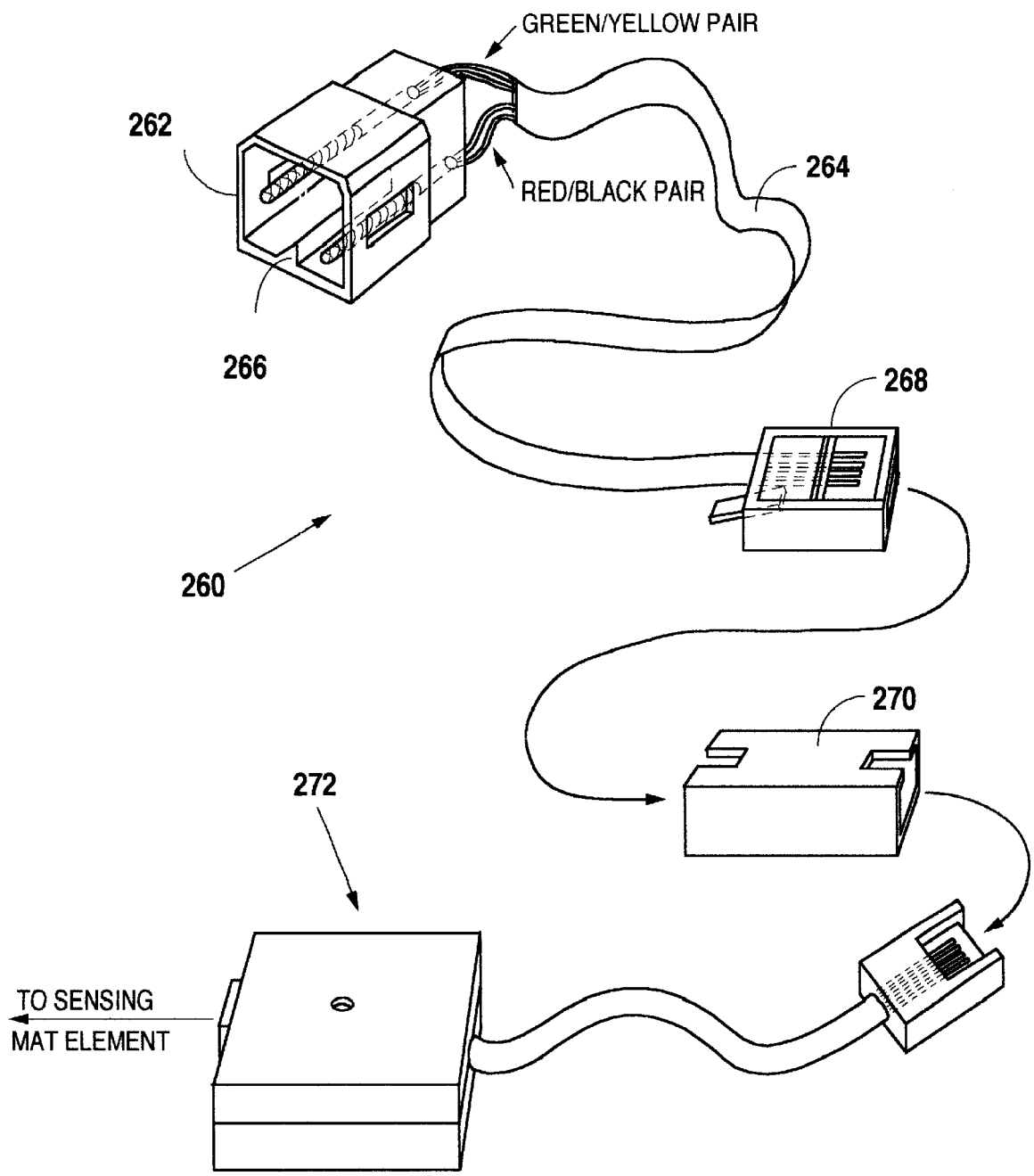
FIG. 20 is an exploded perspective view of an interconnect cord component associated with the system of the present invention.

To permit the interconnection of capacitive sensing elements (such as those described above) with patient occupancy monitoring electronic controls that may already be present on a medical bed (such as those manufactured by Hill-Rom and others), an interface connector is needed and is described in FIG. 20. Interface connector (260) consists of an appropriate female electronic connector (262), namely a Molex Part #03-06-2043, connected to an appropriate length of four conductor modular telephone cord (264). The four conductors of the modular telephone cord (264) are paired and connected red to black and green to yellow and attached to two pins of the female Molex connector (262) in a diagonal manner relative to the locator key (266) of the Molex connector (262). In this manner, the two connecting pins of the Molex connector (262) simulate the standard connection to the medical bed patient occupancy monitoring controls, such as those on a Hill-Rom medical bed, for a single under mattress pressure sensing element.

The distal end of the four conductor modular telephone cord (264) terminates in a four conductor modular telephone plug (268), or alternatively in a four conductor female telephone socket (not shown). Modular telephone plug (268) may be adapted to a four conductor socket through the attachment of a modular telephone cord in-line connector (270).

Through the above described medical bed interface connecting cord, connection between a capacitive based sensing element as described above, or any other "switch" function based pressure sensing element, and medical bed patient occupancy monitoring system, such as those found on Hill-Rom medical beds, may be effected.

The basic patient monitoring system described herein includes a sensor/driver module that generates a frequency shift output as an indication of a capacitance shift in the sensing element. The capacitance shift indicates a change in the presence of the patient adjacent the sensor. To utilize a capacitive sensing element, as described above, a self powered interconnect adapter (272) is located between the frequency shift output of the sensor/driver module as described above, and the input to the "switch" sensing existing medical bed patient occupancy monitor controls. This interconnect adapter (272) employs the same functional electronics described in the control/monitor module of the above referenced embodiment, but excludes the incorporation of system controls, function indicator lights or audible alarms. Its function is to convert the variable frequency output from sensor/driver module associated with the capacitance based sensor to a "switch" function through an electronic relay activation.

The circuitry of interconnect adapter (272) is straightforward and well known in the art. The circuitry detects and measures the frequency shift associated with the capacitance change measured in the capacitive sensing element and activates or deactivates a relay connection accordingly. The state of this relay connection provides an open circuit or a closed circuit condition in the cabling and connectors to the existing patient occupancy monitor circuitry. In this manner the "switch" function based patient occupancy monitor control electronics embedded in existing medical bed systems such as those manufactured by Hill-Rom are able to perceive and interpret the variable frequency output of the sensor/driver module associated with a capacitance based sensor, as a "switch" function, and to respond accordingly.

It is anticipated that further embodiments and alternative applications of the present invention may be envisioned from the above description and the attached drawings. Since any number of potential applications for identifying the presence or absence of a person or other animate or inanimate object within a particular defined space may be desirable, various modifications of the sensing element and the electronics associated with its use are contemplated. Specific modifications of the geometry of the sensing element shown in the preferred embodiment are immediately discernable from the structures and geometries of the devices and environment within which the sensing element is to be placed. The particular geometries described above are appropriate primarily for patient bed configurations and could easily be adapted to be appropriate to, for example, wheelchair environments or other sitting structures. Likewise, placement of the sensing elements described, with appropriate geometry modifications, could be made in enclosures suitable for retaining animals in veterinary hospital environments. The ability of the system to constantly optimize the capacitance measurement ratio in a manner that distinguishes between occupied and unoccupied states permits significant variations in the placement of the sensing element. Such variations are anticipated and included within the scope of the description of the present invention.

I claim:

1. A modular apparatus for monitoring the presence of a person within a predefined space, the apparatus comprising:
a sensor mat having at least one flexible capacitance sensor, said at least one flexible capacitance sensor comprising a plurality of coplanar conductive elements positioned in spaced relation to one another, said sensor mat being adapted for placement adjacent said person;

a driver/sensor circuit electrically connected to said flexible capacitance sensor of said sensor mat for supplying a voltage between said plurality of conductive elements, detecting a change in capacitance associated with said flexible capacitance sensor in response to a change in position of a person with respect to said flexible capacitance sensor, and generating an output signal having frequency variations representative of said change in capacitance, said driver/sensor circuit being positioned adjacent said plurality of conductive elements to minimize interference from external electromagnetic fields; and a control/monitor module electrically connected to said driver/sensor circuit for receiving said output signal from said driver/sensor circuit, analyzing said output signal to make a determination of whether said output signal is representative of a change in the presence of said person within a predefined space, and generating an alarm signal if said determination is affirmative.

2. The apparatus of claim 1 wherein said conductive elements are longitudinal and arranged in parallel.

3. The apparatus of claim 1 wherein said alarm signal produces a visible alarm.

4. The apparatus of claim 1 wherein said alarm signal produces an audible alarm.

5. The apparatus of claim 4 wherein said control/monitor module comprises a piezoelectric acoustic sounder for providing said audible alarm.

6. The apparatus of claim 1 further comprising a wheelchair mounting clip for mounting said control/monitor module to the seat back of a wheelchair.

7. The apparatus of claim 6 wherein said control/monitor module comprises an outer shell having a slot and wherein said wheelchair mounting clip comprises a first hook portion for sliding over a seat back of a wheelchair and a second hook portion for insertion into said slot.

8. The apparatus of claim 1 further comprising a wall mounting clip for mounting said control/monitor module to a wall.

9. The apparatus of claim 8 where in s aid control/monitor module comprises an outer shell having a slot and wherein said wall mounting clip comprises a back plate for attachment to a wall, a hook structure depending from said back plate, and a lip protruding from said hook structure, said lip being adapted for insertion into said slot to secure said control/monitor module to a wall.

10. The apparatus of claim 8 wherein said control/monitor module comprises an outer shell having a slot and a first hole; wherein said wall mounting clip comprises a back plate for attachment to a wall and a support plate extending from said back plate, said support plate having a second hole therein; said support plate being insertable into said slot of said control/monitor module such that said second hole is aligned with said first hole; and further comprising a locking device insertable through said first and second holes to secure said control/monitor module to a wall.

11. The apparatus of claim 1 further comprising an auxiliary alarm module connected to said control/monitor module for receiving said alarm signal and providing specialized alarms.

12. The apparatus of claim 11 wherein said auxiliary alarm module comprises a loud tone circuit for producing a loud tone in response to said alarm signal, a voice announce circuit for producing a recorded voice message in response to said alarm signal, and a mode select switch for selectively switching between said loud tone circuit and said voice announce circuit.

13. The apparatus of claim 1 further comprising an elapsed time module connected to said control/monitor module, said elapsed time module having a control logic circuit for receiving said alarm signal and detecting changes in status of said alarm signal a clock connected to said control logic circuit for determining the times associated with said changes in status of said alarm signal, and a memory connected to said control logic circuit for recording said times and the status of said alarm signal at said times, thereby providing a record of alarm events and care giver response times.

14. The apparatus of claim 1 further comprising a wireless remote alarm module having a wireless transmitter and a wireless receiver, said wireless transmitter being connected to said control/monitor module for receiving said alarm signal and transmitting a radio frequency signal to said wireless receiver, said wireless receiver having a speaker for generating an alarm tone in response to said radio frequency signal.

15. The apparatus of claim 14 wherein said wireless transmitter includes a manually operable switch for initiating the transmission of said radio frequency signal to said wireless receiver.

16. The apparatus of claim 1 wherein said sensor mat is electrically connected to said driver/sensor circuit with a plurality of snap-on connectors, each of said snap-on connectors comprising a male snap component and a female snap component adapted for respectively sandwiching each of said plurality of coplanar conductive elements of said sensor mat, each of said snap-on connectors further comprising a conductor electrically connecting each of said snap-on connectors to said driver/sensor circuit.

17. A modular apparatus for monitoring the presence of a person within a predefined space on a bed, said bed having a mattress, said apparatus comprising:

a mattress cover having at least one flexible capacitance sensor, said at least one flexible capacitance sensor comprising a plurality of coplanar conductive elements positioned in spaced relation to one another, said mattress cover being adapted for overfitting the mattress such that a person may overlie said plurality of coplanar conductive elements when resting on the bed;

a driver/sensor circuit electrically connected to said flexible capacitance sensor for supplying a voltage between said plurality of conductive elements, detecting a change in capacitance associated with said flexible capacitance sensor in response to a change in position of a person with respect to said flexible capacitance sensor, and generating an output signal having frequency variations representative of said change in capacitance, said driver/sensor circuit being positioned adjacent said plurality of conductive elements to minimize interference from external electromagnetic fields; and a control/monitor module electrically connected to said driver/sensor circuit for receiving said output signal from said driver/sensor circuit, analyzing said output signal to make a determination of whether said output signal is representative of a change in presence of a person within a predefined space, and generating an alarm signal if said determination is affirmative.

18. The apparatus of claim 17 wherein said mattress cover has an underside and said plurality of coplanar conductive elements is disposed on said underside of said mattress cover.

19. The apparatus of claim 17 wherein said plurality of coplanar conductive elements comprises bands of conductive ink deposited on said mattress cover.

20. The apparatus of claim 17 wherein said plurality of coplanar conductive elements comprises a pair of bands spanning the width of said mattress cover.

21. The apparatus of claim 17 wherein said mattress cover has an underside and wherein said plurality of coplanar conductive elements comprises a pair of bands of conductive ink deposited on said underside of said mattress cover, said pair of bands spanning the width of said mattress cover.

22. The apparatus of claim 17 wherein said plurality of coplanar conductive elements comprises bands of conductive threads woven into said mattress cover.

23. A modular apparatus for monitoring the presence of a patient within a predefined space in a hospital, said hospital having an existing switch-based monitor/control unit for monitoring a particular attribute of the patient and generating an alarm signal in response to a preselected condition of said attribute, said hospital further having an existing nurse call system connected to said switch-based monitor/control unit for alerting medical personnel in response to said alarm signal, said apparatus comprising:

- a sensor mat having at least one flexible capacitance sensor, said at least one flexible capacitance sensor comprising a plurality of coplanar conductive elements positioned in spaced relation to one another, said sensor mat being adapted for placement adjacent to a patient;
- a driver/sensor circuit electrically connected to said sensor mat for supplying a voltage between said plurality of conductive elements, detecting a change in capacitance associated with said flexible capacitance sensor in response to a change in position of a patient with respect to said capacitance sensor, and generating an output signal having frequency variations representative of said change in capacitance, said driver/sensor circuit being positioned adjacent said plurality of conductive elements to minimize interference from external electromagnetic fields; and
- an interconnect adapter module electrically interconnected to said driver/sensor circuit and an existing switch-based monitor/control unit for receiving said output signal from said driver/sensor circuit and relaying said output signal to an existing switch-based monitor/control unit;
- wherein the existing switch-based monitor/control unit may be adapted for analyzing said output signal to make a determination of whether said output signal is representative of a change in presence of a patient within a predefined space and generating an alarm signal if said determination is affirmative.

24. A modular apparatus for monitoring the presence of a patient within a predefined space on a hospital bed, said hospital bed having existing switch-based patient occupancy monitoring electronics, said apparatus comprising:

- a sensor mat having at least one flexible capacitance sensor, said at least one flexible capacitance sensor comprising a plurality of coplanar conductive elements positioned in spaced relation to one another, said sensor mat being adapted for placement adjacent the person;
- a driver/sensor circuit electrically connected to said flexible capacitance sensor of said sensor mat for supplying a voltage between said plurality of conductive elements, detecting a change in capacitance associated with said flexible capacitance sensor in response to a change in position of the person with respect to said flexible capacitance sensor, and generating an output signal having frequency variations representative of said change in capacitance, said driver/sensor circuit being positioned adjacent said plurality of conductive elements to minimize interference from external electromagnetic fields; and
- an interface connector electrically connected to said driver/sensor circuit and said existing switch-based patient occupancy monitoring electronics, said interface connector having an electronic relay circuit for receiving said output signal from said driver/sensor circuit, analyzing said output signal to make a determination of whether said change in capacitance is representative of a change in presence of the patient within a predefined space, and activating a relay connection to the existing switch-based patient occupancy monitoring electronics if said determination is affirmative.

* * * * *